United States Patent
Spears et al.

(10) Patent No.: US 11,214,836 B2
(45) Date of Patent: Jan. 4, 2022

(54) METHODS AND DEVICES FOR PREDICTING ANTHRACYCLINE TREATMENT EFFICACY

(71) Applicant: Ontario Institute for Cancer Research, Toronto (CA)

(72) Inventors: Melanie Spears, Etobicoke (CA); John Bartlett, Toronto (CA); Fouad Yousif, Burlington (CA); Paul Boutros, Toronto (CA)

(73) Assignee: Ontario Institute for Cancer Research, Toronto (CA)

( * ) Notice: Subject to any disclaimer, the term of this patent is extended or adjusted under 35 U.S.C. 154(b) by 353 days.

(21) Appl. No.: 15/325,472

(22) PCT Filed: Jul. 15, 2015

(86) PCT No.: PCT/CA2015/050660
§ 371 (c)(1),
(2) Date: Jan. 11, 2017

(87) PCT Pub. No.: WO2016/008048
PCT Pub. Date: Jan. 21, 2016

(65) Prior Publication Data
US 2017/0175204 A1     Jun. 22, 2017

Related U.S. Application Data

(60) Provisional application No. 62/024,729, filed on Jul. 15, 2014.

(51) Int. Cl.
| | |
|---|---|
| *C12Q 1/6886* | (2018.01) |
| *A61K 31/704* | (2006.01) |
| *C12M 1/34* | (2006.01) |
| *C12Q 1/68* | (2018.01) |
| *G01N 33/574* | (2006.01) |
| *A61K 38/12* | (2006.01) |
| *A61K 31/407* | (2006.01) |
| *A61K 31/136* | (2006.01) |

(52) U.S. Cl.
CPC .......... *C12Q 1/6886* (2013.01); *A61K 31/136* (2013.01); *A61K 31/407* (2013.01); *A61K 31/704* (2013.01); *A61K 38/12* (2013.01); *C12M 1/34* (2013.01); *C12Q 1/68* (2013.01); *G01N 33/57415* (2013.01); *G01N 33/57484* (2013.01); *C12Q 2600/106* (2013.01); *C12Q 2600/158* (2013.01); *G01N 2800/52* (2013.01)

(58) Field of Classification Search
CPC .................................................. C12Q 1/6886
USPC ........................................................ 435/6.1
See application file for complete search history.

(56) References Cited

U.S. PATENT DOCUMENTS

2009/0215054 A1* 8/2009 Carter ................. C12Q 1/6886
                                                                    435/6.14
2012/0052079 A1    3/2012 Richardson et al.

FOREIGN PATENT DOCUMENTS

| WO | WO-2007/085497 A2 | 8/2007 |
| WO | WO-2011/005384 A2 | 1/2011 |
| WO | WO-2014/085653 A1 | 6/2014 |

OTHER PUBLICATIONS

Park et al (Breast Cancer Research and Treatment, 2006, 99: 9-17).*
Frasci et al (Annals of Oncology, 2009, 20: 1185-1192).*
Santarpia et al (The Oncologist, 2013, 18: 1063-1073).*
Arai et al (Liver Int, 2009, 29(1): Abstract).*
International Search Report and Written Opinion for International Patent Application No. PCT/CA2015/050660, dated Oct. 14, 2015 (15 pages).
Munro et al., "Is TIMP-1 immunoreactivity alone or in combination with other markers a predictor of benefit from anthracyclines in the BR9601 adjuvant breast cancer chemotherapy trial?," Breast Cancer Res. 15(2):R31 (2013) (8 pages).
Tsai et al., "Up-regulation of hepatoma-derived growth factor facilitates tumor progression in malignant melanoma," PLoS One. 8(3):e59345 (2013) (9 pages).
International Preliminary Report on Patentability for International Patent Application No. PCT/CA2015/050660, dated Jan. 17, 2017 (9 pages).
Extended European Search Report for European Application No. 15822898.1, dated Jan. 25, 2018 (11 pages).
Munro et al., "Chromosome instability and benefit from adjuvant anthracyclines in breast cancer," Br J Cancer. 107(1):71-4 (2012).
Munro et al., "Targeting anthracyclines in early breast cancer: new candidate predictive biomarkers emerge," Oncogene. 29(38):5231-40 (2010).
Pritchard et al., "Chromosome 17 centromere (CEP17) duplication as a predictor of anthracycline response: evidence from the NCIC Clinical Trials Group (NCIC CTG) MA.5 Trial," Breast Cancer Res Treat. 131(2):541-51 (2012).

* cited by examiner

*Primary Examiner* — Sean E Aeder
(74) *Attorney, Agent, or Firm* — Norton Rose Fulbright US LLP

(57) ABSTRACT

The invention features methods, devices, and kits for predicting the responsiveness of a cancer patient (e.g., a breast cancer patient, such as a grade 1, 2, or 3 breast cancer patient) to anthracycline treatment by determining the expression levels of four chromosomal instability (CIN) genes including HDGF, KIAA0286, RFC4, and MSH6, collectively referred to as CIN4. Patients that have a low CIN4 score benefit from anthracycline treatment compared patients with a high CIN4 score.

34 Claims, 3 Drawing Sheets
Specification includes a Sequence Listing.

METHODS AND DEVICES FOR PREDICTING ANTHRACYCLINE TREATMENT EFFICACY

BACKGROUND

Meta-analyses performed by the Early Breast Cancer Trialists Collaborative Group (EBCTTCG) demonstrate a significant increase in disease free and overall survival through the addition of anthracyclines to polychemotherapy (EBCTTCG, *Lancet* 365:1687-717, 2005). However, these meta-analyses also show that despite the success of modern chemotherapy approaches, 20-30% of women diagnosed with early stage disease relapse and progress to metastatic breast cancer (MBC), for which therapeutic options are limited and palliative, while around 60-70% of women are treated effectively by non-anthracycline containing therapies. It is therefore essential to select the subset of patients who would receive the optimal overall benefit from anthracycline therapy and to identify molecular pathways driving resistance. Various markers that may predict anthracycline benefit have been explored (HER2, TOP2A, CEP17 and TIMP1) with limited success (Pritchard et al., *New England J. Med.* 354:2103-2111, 2006; Bartlett et al., *Cancer Res.* 69:364S, 2009; DiLeo et al., *Cancer Res.* 69:99S, 2009; Bartlett et al., *Lancet Oncol.* 11:266-274, 2010; Pritchard et al., *Breast Cancer Res. Treat.* 131:541-551, 2012). To date, CEP17 (duplication of the peri-centromeric α-satellite region of chromosome 17) is the only marker that has shown unifying results across a number of clinical trials (Bartlett et al., *Cancer Res.* 69:364S, 2009; Pritchard et al., *Breast Cancer Res. Treat.* 131:541-551, 2012; Bartlett et al., *Ejc Supplements* 8:121, 2010). Thus, CEP17 is an independent predictor of anthracycline benefit. One of the caveats with this is that CEP17 duplication has no known biological function. The functional pathway related to anthracycline benefit in CEP17 duplicated tumors remains unknown. There is evidence (Munro et al., *Br. J. Cancer* 107:71-74, 2012) that suggests CEP17 acts as a surrogate biomarker for chromosome instability. A previous in silico study demonstrated chromosome instability (CIN) was associated with patient outcome.

Chromosomal instability describes genomic instability at the karyotypic level that results in alterations in chromosomal number or structure. Several mechanisms have been implicated in chromosomal instability, including compromised spindle assembly checkpoint (SAC), sister chromatid cohesion defects, additional centrosomes, and abnormal spindle kinetochore attachments. Premitotic mechanisms can also include defects in DNA repair and replication pathways. Chromosomal instability is a driver of intercellular variation and is associated with poor prognosis in many patients with solid tumors (Carter et al., *Nat. Genet.* 38:1043-1048, 2006; Habermann et al. *Int. J. Cancer* 124: 1552-1564, 2009). The top 25 and top 70 gene signatures associated with chromosomal instability, which were identified as predictive of clinical outcome based on in silico analysis of mRNA levels from cancer data sets, have been designated the "CIN25" and "CIN70" signatures, respectively (Carter et al., *Nat. Genet.* 38:1043-1048, 2006). The CIN70 chromosomal instability signature incorporates many genes whose mRNA expression levels correlate with cell proliferation, and have a role in the cell cycle. Furthermore high CIN70 signature expression was associated with paclitaxel resistance in ovarian cancers. The CIN25 signature includes the top 25 ranked genes of 70 gene signature (CIN70). The CIN25 signature was demonstrated to be predictive of anthracycline sensitivity. However, power calculations suggest that large sample sizes (e.g., 3000 samples) may be required for CIN25 signature to be statistically powered to validate the treatment by marker hazard ratio observed for this marker. CIN70 was originally linked to taxane resistance in ovarian and colorectal cancer and to chromosomal instability. Investigation of the CIN70 gene signature in a larger dataset such as National Epirubicin Adjuvant Trial (NEAT) may fully elucidate the role of CIN70 in anthracycline sensitivity. High CIN scores are associated with poor clinical outcome in breast, lung and brain tumors. Research from our group links the predictive effect of CEP17 in vivo, to CIN which itself is predictive of anthracycline benefit in the BR9601 trial (Munro et al., *Br. J. Cancer* 107:71-74, 2012).

Several studies have demonstrated correlations between grade and chromosomal instability. A study performed in our lab using fluorescence in situ hybridization (FISH) demonstrated that tumors with a high percentage of chromosomal instability are correlated with high grade (Munro et al., *Br J Cancer* 107:71-74, 2012). It has been suggested that low-grade and intermediate grade tumors have fewer structural genomic aberrations and numerical aberrations in whole chromosomes (A'Hern et al., *Nat Rev Clin Oncol* 10:357-364, 2013; Dellas et al., *Clin Cancer Res* 8:1210-1216, 2002). A study performed by Szasz and colleagues (23) identified four CIN genes, AURKA, FOXM1, TOP2A, and TPX2, from the CIN70 signature based on the high level of correlation with histological tumor grade and in silico expressions of these genes. The CIN score of these four genes was able to stratify grade 2 breast cancer patients into good and poor prognostics cohorts even better than Ki67 and the mitotic index (Szasz et al., *PLoS One* 8:e56707, 2013).

There exists a need for improved methods for predicting treatment outcomes in cancer patient populations.

SUMMARY OF THE INVENTION

The methods and devices of the invention feature determining a four-gene-based signature (CIN4) that can be used to predict a cancer patient's responsiveness to anthracycline treatment. The four genes or biomarkers included in the CIN4 signature are HDGF, KIAA0286, RFC4, and MSH6. The expression level of one or more, or all of these biomarkers can be used to predict the likelihood a cancer patient will respond to anthracycline treatment.

In a first aspect, the invention features a method of predicting the responsiveness of a cancer patient to anthracycline treatment including determining the level of expression of at least one biomarker selected from the group consisting of HDGF, KIAA0286, RFC4, and MSH6 in a sample from the patient, in which the level of expression of the biomarker indicates whether the patient is responsive to the treatment.

In a second aspect, the invention features a method of predicting the responsiveness of a cancer patient to anthracycline treatment including determining the level of expression of a biomarker having all or a portion of the sequence of SEQ ID NO: 1 in a sample from the patient, in which the level of expression of the biomarker indicates whether the patient is responsive to the treatment.

In a third aspect, the invention features a method of predicting the responsiveness of a cancer patient to anthracycline treatment including determining the level of expression of a biomarker having all or a portion of the sequence of SEQ ID NO: 2 in a sample from the patient, in which the level of expression of the biomarker indicates whether the patient is responsive to the treatment.

In a fourth aspect, the invention features a method of predicting the responsiveness of a cancer patient to anthracycline treatment including determining the level of expression of a biomarker having all or a portion of the sequence of SEQ ID NO: 3 in a sample from the patient, in which the level of expression of the biomarker indicates whether the patient is responsive to the treatment.

In a fifth aspect, the invention features a method of predicting the responsiveness of a cancer patient to anthracycline treatment including determining the level of expression of a biomarker having all or a portion of the sequence of SEQ ID NO: 4 in a sample from the patient, in which the level of expression of the biomarker indicates whether the patient is responsive to the treatment.

In a sixth aspect, the invention features a method of predicting the responsiveness of a cancer patient to anthracycline treatment including determining the level of expression of a biomarker having all or a portion of the sequence of any one of SEQ ID NOs: 1-4 in a sample from the patient, in which the level of expression of the biomarker indicates whether the patient is responsive to the treatment.

In an embodiment, the method of predicting the responsiveness of a cancer patient to anthracycline treatment includes: a) determining the level of expression of at least one biomarker selected from the group consisting of HDGF, KIAA0286, RFC4, and MSH6 in a sample from the cancer patient, and b) i) comparing the level of expression of the biomarker in the sample from the cancer patient to the level of expression of the biomarker in a sample from a first reference patient known to be responsive to anthracycline treatment, or ii) comparing the level of expression of the biomarker in the sample from the cancer patient to the level of expression of the biomarker in a sample from a second reference patient known to be non-responsive to anthracycline treatment, in which a determination that the level of expression of the biomarker in the sample from the cancer patient is similar (e.g., exhibits the same trend or is statistically related) to the level of expression of the biomarker in the sample from the first reference patient indicates that the cancer patient is responsive to the anthracycline treatment, or in which a determination that the level of expression of the biomarker in the sample from the cancer patient is dissimilar (e.g., exhibits an opposite trend or is statistically unrelated) to the level of expression of the biomarker in the sample from the second reference patient indicates that the cancer patient is responsive to the anthracycline treatment. Alternatively, a determination that the level of expression of the biomarker in the sample from the cancer patient is similar (e.g., exhibits the same trend or is statistically related) to the level of expression of the biomarker in the sample from the second reference patient indicates that the cancer patient will likely be non-responsive to the anthracycline treatment In another embodiment, the method of predicting the responsiveness of a cancer patient to anthracycline treatment includes: a) determining the level of expression of a biomarker having all or a portion of the sequence of SEQ ID NO: 1, 2, 3, or 4 in a sample from the cancer patient, and b) i) comparing the level of expression of the biomarker in the sample from the cancer patient to the level of expression of the biomarker in a sample from a first reference patient known to be responsive to anthracycline treatment, or ii) comparing the level of expression of the biomarker in the sample from the cancer patient to the level of expression of the biomarker in a sample from a second reference patient known to be non-responsive to anthracycline treatment, in which a determination that the level of expression of the biomarker in the sample from the cancer patient is similar (e.g., exhibits the same trend or is statistically related) to the level of expression of the biomarker in the sample from the first reference patient indicates that the cancer patient is responsive to the anthracycline treatment, or in which a determination that the level of expression of the biomarker in the sample from the cancer patient is dissimilar (e.g., exhibits an opposite trend or is statistically unrelated) to the level of expression of the biomarker in the sample from the second reference patient indicates that the cancer patient is responsive to the anthracycline treatment. Alternatively, a determination that the level of expression of the biomarker in the sample from the cancer patient is similar (e.g., exhibits the same trend or is statistically related) to the level of expression of the biomarker in the sample from the second reference patient indicates that the cancer patient will likely be non-responsive to the anthracycline treatment.

In some embodiments, the sample from the patient is a tissue sample. In particular, the sample is a tumor sample.

In some embodiments, the cancer is a breast cancer. In particular, the cancer is grade 1, 2, or 3.

In some embodiments, the determining of the level of expression of the biomarker occurs in the patient after a cancer treatment (e.g., surgery).

In other embodiments, the determining of the level of expression of the biomarker occurs in the patient prior to a first cancer treatment.

In other embodiments, the determining of the level of expression of the biomarker occurs in the patient after a first cancer treatment, but before a second cancer treatment.

In yet other embodiments, the determining occurs in the patient after a second cancer treatment.

In some embodiments, the treatment includes one or more of surgery, radiation therapy, and chemotherapy. Preferably, the cancer treatment is surgery.

In some embodiments, a high level of expression of one or more, or all, of the biomarkers (e.g., a low CIN4 score) indicates responsiveness to anthracycline treatment.

In some embodiments, the level of expression of the biomarker in the sample may be directly detected using a probe that hybridizes to the nucleic acid molecule encoding the biomarker. In some embodiments, the nucleic acid encoding the biomarker may be labeled with a probe, e.g., a fluorescent molecule (e.g., a non-naturally occurring fluorescent molecule), and detected using fluorescence readout. In other embodiments, the level of expression of the biomarkers in the sample may be detected after amplification of the nucleic acid molecule encoding the biomarker. Methods to detect and quantify the nucleic acid molecules encoding the biomarkers include, but are not limited to, Nanostring technologies or protocols (Nanostring® Technologies, Seattle, Wash., USA; e.g., those described in U.S. Patent Application Nos. US20110201515, US20110229888, and US 20130017971, each of which is incorporated by reference in its entireties) and quantitative reverse transcription-polymerase chain reaction (qRT-PCR).

In a preferred embodiment, the level of expression of the biomarker in the sample is determined by collecting nucleic acid molecules from the sample and using Nanostring technologies or protocols (Nanostring® Technologies, Seattle, Wash., USA) to detect and quantify the nucleic acid molecules.

In other embodiments, the level of expression of the biomarker in the sample is determined by collecting nucleic acid molecules from the sample and, optionally, using a quantitative reverse transcription-polymerase chain reaction (qRT-PCR) to amplify the nucleic acid molecules.

In other embodiments, some methods of the invention further include treating the cancer patient predicted to be responsive to anthracycline treatment with an anthracycline. In particular, the anthracycline is selected from the group consisting of epirubicin, daunorubicin, doxorubicin, idarubicin, valrubicin, actinomycin-D, bleomycin, mitomycin-C, and mitoxantrone, preferably, the anthracycline is epirubicin. In other embodiments, the cancer patient may also be treated with one or more of the chemotherapeutic agents listed in Table 2.

In other embodiments, some methods of the invention further include treating the cancer patient predicted to be non-responsive to anthracycline treatment with a non-anthracycline treatment, such as one or more of the chemotherapeutic agents listed in Table 2.

In some embodiments, the level of expression of the biomarker is determined using a microarray device.

In other embodiments, the methods of the invention include determining the level of expression of the biomarker using a quantitative reverse transcription-polymerase chain reaction.

In some embodiments, the level of expression of the biomarkers, e.g., HDGF, KIAA0286, RFC4, and MSH6, is determined by artificially and detectably labeling nucleic acid molecules in the sample obtained from the cancer patient, e.g., a breast cancer patient, such as grade 1, 2, or 3 breast cancer patient, and measuring the level of expression of the biomarkers, e.g., HDGF, KIAA0286, RFC4, and MSH6, using the artificially and detectably labeled nucleic acid molecules.

In another aspect, the invention features a method of treating a cancer in a cancer patient determined to have a similar level of expression of at least one biomarker selected from the group consisting of HDGF, KIAA0286, RFC4, and MSH6 to the level of expression of the biomarker in a first reference patient known to be responsive to anthracycline treatment, the method includes administering an anthracycline to the cancer patient.

In another aspect, the invention features a method of treating a cancer in a cancer patient determined to have a similar level of expression of a biomarker having all or a portion of the sequence of SEQ ID NO: 1, 2, 3, or 4 to the level of expression of the biomarker in a first reference patient known to be responsive to anthracycline treatment, the method includes administering an anthracycline to the cancer patient.

In some embodiments, the anthracycline is selected from the group consisting of epirubicin, daunorubicin, doxorubicin, idarubicin, valrubicin, actinomycin-D, bleomycin, mitomycin-C, and mitoxantrone. Preferably, the anthracycline is epirubicin.

In some embodiments of this aspect of the invention, the cancer patient is determined to have a similar level of expression of the biomarker to the level of expression of the biomarker in a first reference patient known to be responsive to anthracycline treatment by: a) determining the level of expression of the biomarker in a sample from the cancer patient, b) i) comparing the level of expression of the biomarker in the sample from the cancer patient to the level of expression of the biomarker in a sample from a first reference patient known to be responsive to anthracycline treatment, or ii) comparing the level of expression of the biomarker in the sample from the cancer patient to the level of expression of the biomarker in a sample from a second reference patient known to be non-responsive to anthracycline treatment.

In another aspect, the invention features a device including at least one single-stranded nucleic acid molecule having at least 85% identity to a target nucleic acid molecule having a sequence that is complementary or identical to at least 5 (e.g., at least 10, 15, 20, 25, 30, 35, 40, 45, or 50; preferably at least about 25) consecutive nucleotides of at least one biomarker selected from HDGF, KIAA0286, RFC4, and MSH6 in a sample from a cancer patient, in which at least one single-stranded nucleic acid molecule is sufficient for the detection of the level of expression of the biomarker and allows specific hybridization between the single stranded nucleic acid molecule and the target nucleic acid molecule.

In another aspect, the invention features a device including at least one single-stranded nucleic acid molecule having at least 85% identity to a target nucleic acid molecule having a sequence that is complementary or identical to at least 5 (e.g., at least 10, 15, 20, 25, 30, 35, 40, 45, or 50; preferably at least about 25) consecutive nucleotides of a biomarker having the sequence of SEQ ID NO: 1 in a sample from a cancer patient, in which at least one single-stranded nucleic acid molecule is sufficient for the detection of the level of expression of the biomarker and allows specific hybridization between the single stranded nucleic acid molecule and the target nucleic acid molecule.

In another aspect, the invention features a device including at least one single-stranded nucleic acid molecule having at least 85% identity to a target nucleic acid molecule having a sequence that is complementary or identical to at least 5 (e.g., at least 10, 15, 20, 25, 30, 35, 40, 45, or 50; preferably at least about 25) consecutive nucleotides of a biomarker having the sequence of SEQ ID NO: 2 in a sample from a cancer patient, in which the at least one single-stranded nucleic acid molecule is sufficient for the detection of the level of expression of the biomarker and allows specific hybridization between the single stranded nucleic acid molecule and the target nucleic acid molecule.

In another aspect, the invention features a device including at least one single-stranded nucleic acid molecule having at least 85% identity to a target nucleic acid molecule having a sequence that is complementary or identical to at least 5 (e.g., at least 10, 15, 20, 25, 30, 35, 40, 45, or 50; preferably at least about 25) consecutive nucleotides of a biomarker having the sequence of SEQ ID NO: 3 in a sample from a cancer patient, in which the at least one single-stranded nucleic acid molecule is sufficient for the detection of the level of expression of the biomarker and allows specific hybridization between the single stranded nucleic acid molecule and the target nucleic acid molecule.

In another aspect, the invention features a device including at least one single-stranded nucleic acid molecule having at least 85% identity to a target nucleic acid molecule having a sequence that is complementary or identical to at least 5 (e.g., at least 10, 15, 20, 25, 30, 35, 40, 45, or 50; preferably at least about 25) consecutive nucleotides of a biomarker having the sequence of SEQ ID NO: 4 in a sample from a cancer patient, in which the at least one single-stranded nucleic acid molecule is sufficient for the detection of the level of expression of the biomarker and allows specific hybridization between the single stranded nucleic acid molecule and the target nucleic acid molecule.

In another aspect, the invention features a device including at least one single-stranded nucleic acid molecule having at least 85% identity to a target nucleic acid molecule having a sequence that is complementary or identical to at least 5

(e.g., at least 10, 15, 20, 25, 30, 35, 40, 45, or 50; preferably at least about 25) consecutive nucleotides of a biomarker having the sequence of any one of SEQ ID NOs: 1-4 in a sample from a cancer patient, in which the at least one single-stranded nucleic acid molecule is sufficient for the detection of the level of expression of the biomarker and allows specific hybridization between the single stranded nucleic acid molecule and the target nucleic acid molecule.

In some embodiments, the target nucleic acid molecule has a sequence that is complementary or identical to at least 10 to 100, at least 20 to 100, at least 30 to 100, at least 40 to 100, at least 50 to 100, at least 60 to 100, at least 70 to 100, at least 80 to 100, or at least 90 to 100 consecutive nucleotides.

In some embodiments, at least one single-stranded nucleic acid molecule has a length in the range of 10 to 100 nucleotides.

In some embodiments, the device allowing, when contacted with a diverse population of nucleic acid molecules prepared from a sample under conditions allowing hybridization to occur, the determination of the level of expression of the at least one biomarker.

In some embodiments, the device is a microarray device.

In another aspect, the invention features a method for predicting responsiveness of a cancer patient to anthracycline treatment including determining the level of expression of at least one biomarker in a patient sample using any one of the aforementioned devices of the invention, in which the level of expression of the biomarker is predictive of responsiveness of the cancer patient to anthracycline treatment.

In some embodiments, the sample is a tissue sample. In particular, the sample is a tumor sample.

In some embodiments, the cancer is a breast cancer. In particular, the cancer is grade 1, 2, or 3.

In some embodiments, the determining of the level of expression of the biomarker occurs in the patient after a first cancer treatment. Preferably, the first cancer treatment is surgery.

In other embodiments, the determining of the level of expression of the biomarker occurs in the patient prior to a first cancer treatment.

In other embodiments, the determining of the level of expression of the biomarker occurs in said patient after a first cancer treatment, but before a second cancer treatment.

In yet other embodiments, the determining of the level of expression of the biomarker occurs in said patient after a second cancer treatment.

In some embodiments, the treatment includes any combination of one or more of surgery, radiation therapy, and chemotherapy.

In some embodiments, a high expression level of at least one (or all) of the biomarkers (e.g., a low CIN4 score) indicates responsiveness to anthracycline treatment.

In another aspect, the invention features a kit including reagents for collecting nucleic acid molecules from a sample from a cancer patient, reagents for amplifying the nucleic acid molecules collected from the sample to produce an amplified sample, and at least one device for detecting the level of expression of at least one biomarker having the sequence of any one of SEQ ID NOs: 1-4 in the amplified sample.

In some embodiments, a quantitative reverse transcription-polymerase chain reaction (qRT-PCR) is used to produce the amplified sample.

In some embodiments, the kit further includes instructions for predicting responsiveness of a cancer patient to anthracycline treatment based on the level of expression of the at least one biomarker.

In some embodiments, the device in the kit is any one of the aforementioned devices of the invention.

In other embodiments, the kit further includes instructions for applying nucleic acid molecules collected from the sample to the device, and/or instructions for determining the level of expression of the at least one biomarker by detecting hybridization of the at least one single-stranded nucleic acid molecule to the biomarker or its complement sequence.

In other embodiments, the kit further includes instructions for predicting responsiveness of a cancer patient to anthracycline treatment based on the level of expression of the at least one biomarker as detected using the device.

In another aspect, the invention features a method of predicting the responsiveness of a cancer patient to anthracycline treatment including: a) determining a CIN4 signature of the cancer patient, and b) i) comparing the CIN4 signature of the cancer patient to a CIN4 signature of a first reference patient known to be responsive to anthracycline treatment, or ii) comparing the CIN4 signature of the cancer patient to a CIN4 signature of a second reference patient known to be non-responsive to anthracycline treatment, in which a determination that the CIN4 signature of the cancer patient is similar to the CIN4 signature of the first reference patient indicates that the cancer patient is responsive to the anthracycline treatment, or in which a determination that the CIN4 signature of the cancer patient is dissimilar to the CIN4 signature of the second reference patient indicates that the cancer patient is responsive to the anthracycline treatment.

In some embodiments, a low CIN4 signature predicts a cancer patient to be responsive to anthracycline treatment.

DEFINITIONS

The term "cancer patient" as used herein refers to a subject, e.g., a human subject, who has, or has had a cancer and may or may not have been treated for the cancer (e.g., breast, brain, skin, lung, kidney, prostate, or liver cancer). In particular, the cancer may be breast cancer, e.g., grade 1, 2, or 3 breast cancer.

The term "complement" of a nucleic acid sequence or a "complementary" nucleic acid sequence as used herein refers to an oligonucleotide which is in "antiparallel association" when it is aligned with the nucleic acid sequence such that the 5' end of one sequence is paired with the 3' end of the other.

When complementary nucleic acid sequences form a stable duplex, they are said to be "hybridized" or to "hybridize" to each other or it is said that "hybridization" has occurred. Nucleic acids are referred to as being "complementary" if they contain nucleotides or nucleotide homologues that can form hydrogen bonds according to Watson-Crick base-pairing rules (e.g., G with C, A with T or A with U) or other hydrogen bonding motifs such as for example diaminopurine with T, 5-methyl C with G, 2-thiothymidine with A, inosine with C, pseudoisocytosine with G, etc. Anti-sense RNA may be complementary to other oligonucleotides, e.g., mRNA.

The term "biomarker" as used herein indicates a gene or other portion of a subjects genetic material that is expressed in a form that can be measured (e.g., as an mRNA, microRNA, or protein) and whose expression level is indicative of a patient's response to certain drugs. In particular, the expression level of at least one biomarkers selected from HDGF, KIAA0286, RFC4, and MSH6 (SEQ ID NOs: 1-4) may be used to predict a cancer patient's response to anthracycline treatment.

The term "microarray" as used herein means a device employed by any method that quantifies one or more subject oligonucleotides, e.g., DNA or RNA, or analogues thereof, at a time. In a preferred embodiment, one or more subject oligonucleotides, e.g., DNA or RNA, cDNA, or analogues thereof, are quantified using any method or device (e.g., the Nanostring protocol (Nanostring® Technologies, Seattle, Wash., USA)). For example, many microarrays, including those made by Nanostring® Technologies and Affymetrix, use several probes for determining the expression of a single gene. The DNA microarray may contain oligonucleotide probes that may be, e.g., full-length cDNAs complementary to an RNA or cDNA fragments that hybridize to part of an RNA. The DNA microarray may also contain modified versions of DNA or RNA, such as locked nucleic acids or LNA. Exemplary RNAs include mRNA, miRNA, and miRNA precursors. Exemplary microarrays also include a "nucleic acid microarray" having a substrate-bound plurality of nucleic acids, hybridization to each of the plurality of bound nucleic acids being separately detectable. The substrate may be solid or porous, planar or non-planar, unitary or distributed. Exemplary nucleic acid microarrays include all of the devices so called in Schena (ed.), DNA Microarrays: A Practical Approach (Practical Approach Series), Oxford University Press (1999); Nature Genet. 21(I) (suppl.): 1-60 (1999); Schena (ed.), Microarray Biochip: Tools and Technology, Eaton Publishing Company/Bio-Techniques Books Division (2000). Additionally, exemplary nucleic acid microarrays include substrate-bound plurality of nucleic acids in which the plurality of nucleic acids are disposed on a plurality of beads, rather than on a unitary planar substrate, as is described, inter alia, in Brenner et al., Proc. Natl. Acad. Sci. USA 97(4): 1665-1670 (2000). Examples of nucleic acid microarrays may be found in U.S. Pat. Nos. 6,391,623, 6,383,754, 6,383,749, 6,380,377, 6,379,897, 6,376,191, 6,372,431, 6,351,712 6,344,316, 6,316,193, 6,312,906, 6,309,828, 6,309,824, 6,306,643, 6,300,063, 6,287,850, 6,284,497, 6,284,465, 6,280,954, 6,262,216, 6,251,601, 6,245,518, 6,263,287, 6,251,601, 6,238,866, 6,228,575, 6,214,587, 6,203,989, 6, 171,797, 6,103,474, 6,083,726, 6,054,274, 6,040,138, 6,083,726, 6,004,755, 6,001,309, 5,958,342, 5,952, 180, 5,936,731, 5,843,655, 5,814,454, 5,837,196, 5,436,327, 5,412,087, 5,405,783, the disclosures of which are incorporated herein by reference in their entireties.

Exemplary microarrays may also include "peptide microarrays" or "protein microarrays" having a substrate-bound plurality of polypeptides, the binding of a oligonucleotide, a peptide, or a protein to each of the plurality of bound polypeptides being separately detectable. Alternatively, the peptide microarray, may have a plurality of binders, including but not limited to monoclonal antibodies, polyclonal antibodies, phage display binders, yeast 2 hybrid binders, aptamers, which can specifically detect the binding of specific oligonucleotides, peptides, or proteins. Examples of peptide arrays may be found in WO 02/31463, WO 02/25288, WO 01/94946, WO 01/88162, WO 01/68671, WO 01/57259, WO 00/61806, WO 00/54046, WO 00/47774, WO 99/40434, WO 99/39210, WO 97/42507 and U.S. Pat. Nos. 6,268,210, 5,766,960, 5,143,854, the disclosures of which are incorporated herein by reference in their entireties.

The term "CIN4 score" is used to indicate and predict the responsiveness of a cancer patient (e.g., breast cancer patient, such as grade 1, 2, or 3 breast cancer patient) to anthracycline treatment. A low CIN4 score relates to high gene expressions of one or more (e.g., all four) genes in the CIN4 signature (HDGF, KIAA0286, RFC4, and MSH6) and indicates responsiveness of the cancer patient to anthracycline treatment. A high CIN4 score relates to low expressions of one or more (e.g., all four) genes in the CIN4 signature (HDGF, KIAA0286, RFC4, and MSH6) and indicates non-responsiveness of the cancer patient to anthracycline treatment.

The term "treatment" or "medical treatment" means administering to a subject or living organism or exposing to a cell or tumor a compound (e.g., a drug, a protein, an antibody, an oligonucleotide, a chemotherapeutic agent (e.g., anthracycline), or a radioactive agent) or some other form of medical intervention (e.g., cryotherapy and radiation therapy) that can be used to treat or prevent cancer (e.g., breast cancer) or the symptoms of cancer. Radiation therapy includes the administration to a patient of radiation generated from sources such as particle accelerators and related medical devices that emit X-radiation, gamma radiation, or electron (beta radiation) beams. A treatment may further include surgery, e.g., to remove or excise a tumor from a subject or living organism.

DETAILED DESCRIPTION OF THE INVENTION

CIN4 Signature is a Predictive Marker of Anthracycline Benefit

We have discovered that a four-gene-based signature (CIN4) is associated with a cancer patient's response to anthracycline treatment. The CIN4 signature includes the expression levels of one or more, or all of the genes HDGF, KIAA0286, RFC4, and MSH6. In multivariate regression analysis, the CIN4 signature conferred predictive responsiveness to anthracycline treatment. Interestingly, three of the four genes in our CIN4 signature are involved in DNA repair/DNA-binding activity. Anthracyclines are thought to exert their actions by intercalation with DNA, generation of free radicals, and crosslinking DNA to proteins. Therefore, dysregulation of genes involved in DNA repair leads to anthracycline sensitivity.

We discovered that grade 3 breast cancer patients with a high level of CIN benefited from anthracycline therapy. It is possible that low grade tumors are more susceptible to a taxane treatment while higher grade tumors are sensitive to anthracycline treatment. A previous study has demonstrated a high level of CIN70 gene expression is associated with paclitaxel resistance (Swanton et al., Proc Natl Acad Sci. 106:8671-8676, 2009).

In some embodiments, the CIN4 signature is an independent predictor of anthracycline sensitivity. In other embodiments, the combination of chromosomal instability and high tumor grade may predict anthracycline sensitivity and taxane resistance.

Correlation of CIN25 or CIN70 and Clinicopathological Parameters

We successfully analysed 282 of 321 (87.9%) and 421 of 440 (95.7%) tumors from BR9601 and MA.5, respectively. High CIN70 and CIN25 scores were defined as above the median as previously described (Carter et al., Nat Genet 38:1043-1048, 2006). High CIN70 and CIN25 scores were associated with age (p<0.0001), grade (p<0.0001), PgR negativity (p<0.0001), and ER negativity (p<0.0001), but not with tumor size, nodal status, or HER2 status.

CIN Signature as a Prognostic Marker for Overall Survival (OS) and Distant Recurrence-Free Survival (DRFS)

Figure 1:
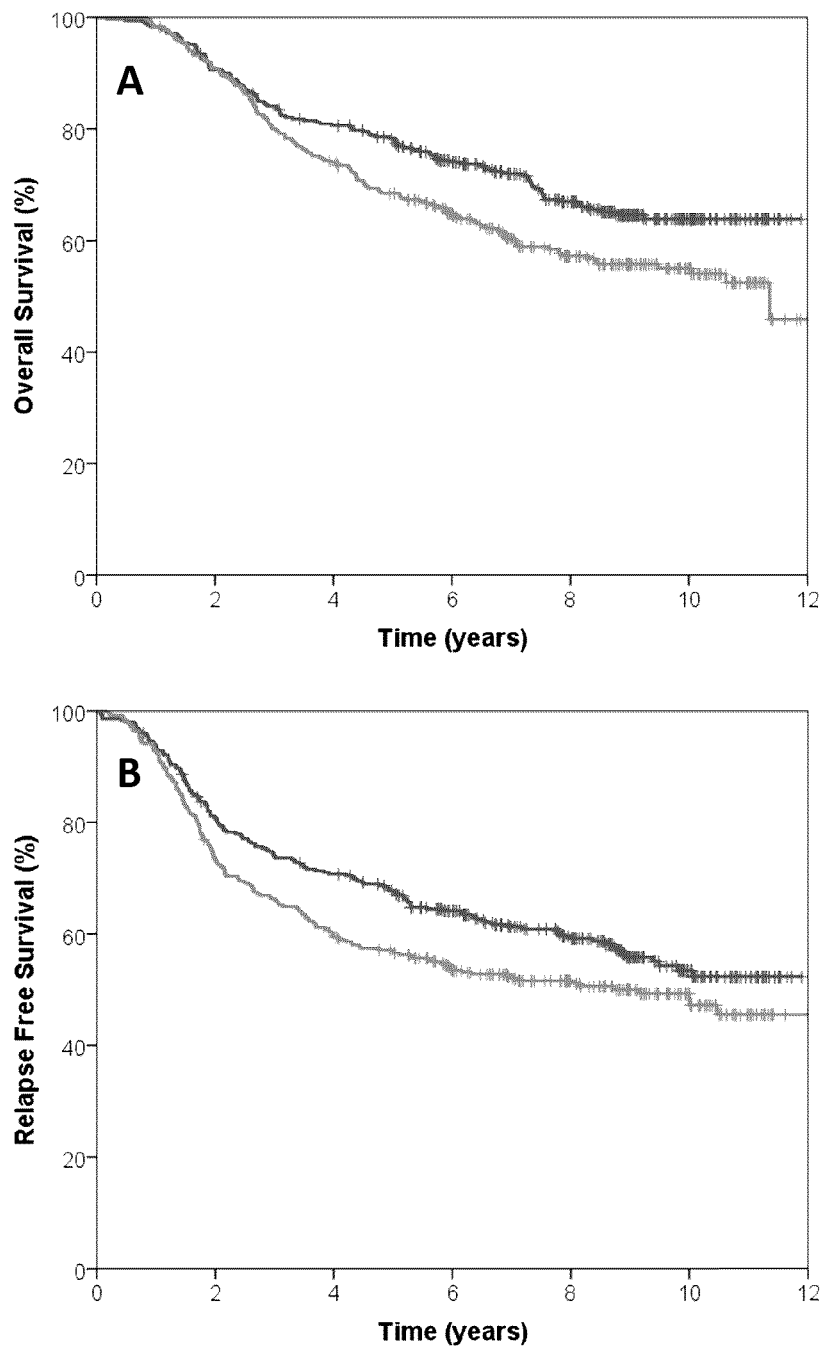
FIG. 1 shows graphs of Kaplan-Meier survival curves for low CIN25 score (lower line) and high CIN25 score (higher line) for overall survival (A) and distant relapse free survival (B).

The prognostic significance of CIN25 and CIN70 was tested on the entire patient cohort, irrespective of allocated adjuvant chemotherapy. No significant association between CIN70 expression and OS or DRFS was evident. Tumors with high CIN25 scores were associated with reduced OS (HR: 0.69, 95% CI 0.54-0.88, p=0.003, FIG. 1A) and DRFS (HR: 0.70, 95% CI 0.60-0.90, p=0.004, FIG. 1B). After multivariate analysis and adjustment for nodal status, grade, size, age, HER2, ER, and PgR status, high CIN25 score was not an independent predictor for OS or DRFS.

CIN Signature as a Biological Marker for Responsiveness to Anthracycline Treatment We analysed the differential effects of the CIN signatures on OS and DRFS between patients receiving anthracycline treatment (E-CMF) and those given CMF alone by assessing hazard ratios. No significant differential benefit from E-CMF treatment was demonstrated between patients whose tumors had high or low CIN70 expression (Table 1)

In univariate analysis, patients whose tumors had high CIN25 gene expression scores had a decreased risk of distant relapse (HR: 0.74, 95% CI 0.54-0.99, p=0.046) when treated with E-CMF compared with patients treated with CMF alone (Table 1). There was no apparent benefit of E-CMF vs CMF noted in patients with low CIN25 scores for DRFS (HR: 0.87, 95% CI 0.61-1.21, p=0.374). In a multivariate analysis with adjustment for size, nodal status, ER, pathological grade, HER2, CIN25, treatment and CIN25*treatment (a marker by treatment interaction test; e.g., McShane, BMC Medicine 10:52, 2012, and Mandrekar et al., Journal of clinical Oncology 27:4027, 2009) showed only pathological grade, nodal status, tumor size, and polysomy to be significant predictors of outcome. No significant differential benefit from E-CMF treatment was demonstrated between patients whose tumors had high or low CIN25 expression for OS (Table 1). The hazard ratio for treatment marker effect of CIN25 was 0.86 (95% CI 0.53-1.40, p=0.549) for OS and 0.86 (95% CI 0.54-1.36, p=0.519) (Table 1).

CIN Signature as a Biological Marker for Responsiveness to Anthracycline Treatment in Grade 3 Patients Previous research identified a significant association between CIN gene expression and grade 3 tumors (Carter et al., Nat Genet 38:1043-1048, 2006). Therefore, an exploratory analysis was performed on patients that were pathological grade 3 only. We analysed the differential effects of the CIN signatures on OS and DRFS between patients receiving anthracycline treatment (E-CMF) and those given CMF alone by assessing hazard ratios.

Figure 2:
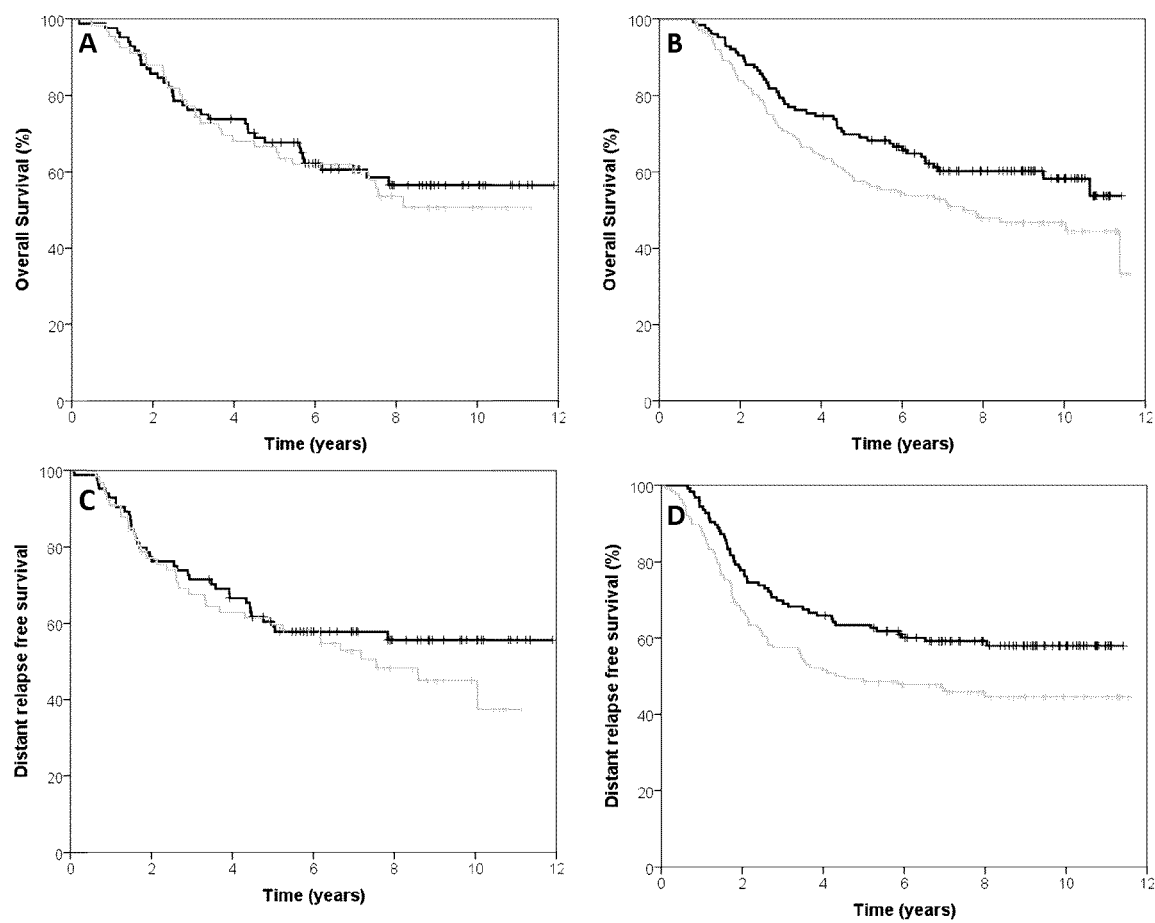
FIG. 2 shows graphs of Kaplan-Meier survival curves for epirubicin plus cyclophosphamide, methotrexate and fluorouracil (E-CMF) (higher line) and CMF (lower line) treated low CIN25 score (A, C) or high CIN25 score (B, D) for overall survival (A, B) and distant relapse free survival (C, D).

In univariate analysis, patients whose tumors had high CIN25 gene expression scores had a reduced risk of distant relapse (HR: 0.66, 96% CI 0.46-0.94, p=0.021) and increased OS (HR: 0.73, 95% CI 0.57-0.95, p=0.05) when treated with E-CMF compared with patients treated with CMF alone (FIG. 2, Table 1). No significant benefit from E-CMF treatment versus CMF treatment was demonstrated in patients with tumors exhibiting low CIN25 gene expression (Table 1). In patients with grade 1 and 2 tumors, no significant benefit from E-CMF treatment versus CMF treatment was demonstrated with either high or low CIN25 gene expression scores (Table 1). The hazard ratio for treatment marker effect of CIN25 in grade 3 tumors was 0.78 (95% CI 0.42-1.43, p=0.413) for OS and 0.81 (95% CI 0.45-1.46, p=0.479) (Table 1).

TABLE 1

Hazard ratios for overall survival and distant relapse free survival comparing epirubicin plus cyclophosphamide, methotrexate and fluorouracil (E-CMF) with CMF alone by biomarker status.

| | Low Biomarker | | High Biomarker | | Treatment*Marker Test for | |
|---|---|---|---|---|---|---|
| | HR | 95% CI | HR | 95% CI | HR | Interaction P |
| Overall Survival (OS) | | | | | | |
| CIN70 | 0.82 | 0.57-1.17 | 0.82 | 0.59-1.14 | 0.99 | 0.977 |
| CIN25 | 0.87 | 0.61-1.29 | 0.76 | 0.56-1.05 | 0.86 | 0.549 |
| CIN25 in grade 3 | 0.91 | 0.55-1.48 | 0.70 | 0.41-1.36 | 0.78 | 0.413 |
| CIN25 in grade 1&2 | 0.74 | 0.41-1.36 | 1.27 | 0.58-2.80 | 1.76 | 0.266 |
| Distant Relapse Free Survival (DRFS) | | | | | | |
| CIN70 | 0.79 | 0.57-1.10 | 0.79 | 0.58-1.08 | 0.97 | 0.904 |
| CIN25 | 0.85 | 0.61-1.21 | 0.74 | 0.54-0.99 | 0.86 | 0.519 |
| CIN25 in grade 3 | 0.81 | 0.51-1.30 | 0.66 | 0.46-0.94 | 0.81 | 0.479 |
| CIN25 in grade 1&2 | 0.85 | 0.50-1.43 | 1.12 | 0.58-2.12 | 1.30 | 0.541 |

CIN4 Signature Predicts Responsiveness to Anthracycline Treatment

In order to select a more limited set of genes that reflects CIN, we used the merged clinical cohort (containing both BR9601 and MA.5). The cohort was split into anthracycline treated and CMF treated cohorts. The patients were clustered using the expression profile of the 70 genes, which led to nine clusters. A multivariate Cox model was fit for each gene, adjusting for clinical variables including HER2, ER, PgR, tumor size, grade, and nodal status. The top genes from each expression cluster, with the most significant p-value in the anthracycline treated cohort and a non-significant CMF cohort, were selected to make a list of 20 genes.

Figure 3:
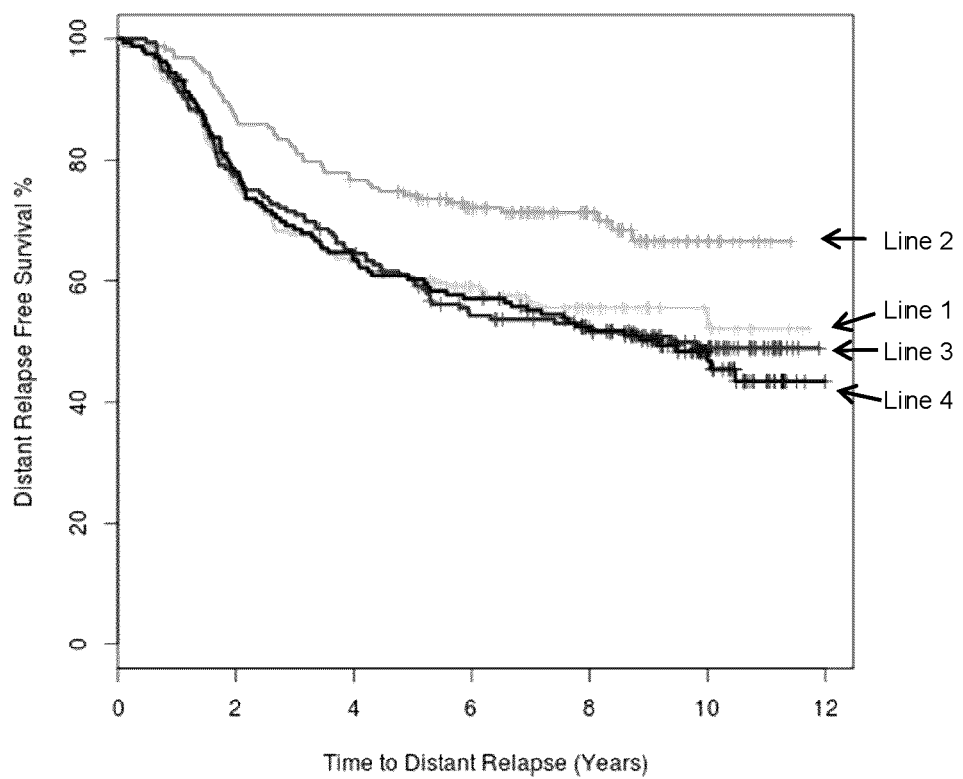
FIG. 3 shows a graph of Kaplan-Meier survival curve for low CIN4 score treated with epirubicin plus cyclophosphamide, methotrexate and fluorouracil (E-CMF) (Line 2), high CIN4 score treated with E-CMF (Line 3), low CIN4 score treated with CMF (Line 1) and high CIN4 score treated with CMF (Line 4) for distant relapse free survival.

From this list of 20 genes, all possible combinations of 2, 3, 4, and 5 gene signatures were examined (210, 1330, 5985 and 20349 combinations, respectively) and bootstrapped 100 times, with the median area under the curve (AUC) noted. In each bootstrap, the treatment cohort was split into 60% training and 40% test sets. The AUC was calculated from the test sets and the gene signature selected had the greatest AUC and had four genes, HDGF, KIAA0286, RFC4, and MSH6, termed the CIN4 signature. A multivariate Cox regression was fit using the 4 genes, adjusting for the same clinical variables mentioned above. A CIN4 score was generated using the expression values of the 4 genes, weighted by their regression coefficients. Patients that have a low CIN4 score benefit from anthracycline treatment compared to high CIN4 score (HR 2.72, 95% Cl 1.48-5.02, p=0.001) (FIGS. 2 and 3). No significant benefit with CMF treatment was observed in either low or high CIN4 score. The hazard ratio for treatment marker effect of CIN4 was 0.35 (95% CI 0.15-0.79, p=0.01) for DRFS.

Methods of Determining Gene Expression and CIN4 Signature Score

In some embodiments, formalin-fixed paraffin embedded (FFPE) tissue samples may be used. In other embodiments, cell or tissue samples (e.g., tissue samples from tumors) taken from patients (e.g., cancer patients, such as breast cancer patients (e.g., grade 1, 2, or 3 breast cancer patients)) may be snap frozen in liquid nitrogen until processing or by other methods known in the art. Total RNA may be extracted from cell or tissue samples using one of the commercially available kits, e.g., preferably RecoverAll Total Nucleic Acid Isolation kit (Life Technologies), or using agents well known in the art, e.g., Trizol Reagent.

The expression levels of the various biomarkers, e.g., one or more (e.g., all) of the four genes in the CIN4 signature (HDGF, KIAA0286, RFC4, and MSH6), using, e.g., isolated RNA, may be determined using procedures, such as a microarray or other known device or platform and quantitative reverse transcriptase polymerase chain reaction (qRT-PCR), that can be used to measure the level of biomarkers expression in a sample. In some embodiments, microarray and qRT-PCR may be performed in combination. Alternatively, the method may determine the expression levels of one or more of the four genes (HDGF, KIAA0286, RFC4, and MSH6) in the CIN4 signature using isolated proteins corresponding to the product of these genes.

A microarray of the invention may include one or more oligonucleotide probes that have nucleotide sequences that are identical to or complementary to, e.g., at least 5, 8, 12, 20, 25, 30, 40, 60, 80, 100, 150, or 200 consecutive nucleotides (or nucleotide analogues) of the biomarkers, e.g., HDGF, KIAA0286, RFC4, and MSH6. The oligonucleotide probes may be, e.g., 5-20, 25, 5-50, 50-100, or over 100 nucleotides long. The oligonucleotide probes may be deoxyribonucleic acids (DNA) or ribonucleic acids (RNA). Additionally, probes employed on microarrays of the invention may also include proteins, peptides, or antibodies that selectively bind any of the oligonucleotide sequences or their complementary sequences of a polypeptide encoded by the gene or mRNA of HDGF, KIAA0286, RFC4, or MSH6.

Procedures for performing qRT-PCR are described in, e.g., U.S. Pat. No. 7,101,663 and U.S. Patent Application Nos. 2006/0177837 and 2006/0088856, each of which is incorporated herein by reference in its entireties.

The resulting gene or protein expression measurements are further processed and statistically analyzed as described further herein. A CIN4 signature score is calculated using statistical analyses described in Example 4.

Identifying a Subpopulation of Patients Sensitive to a Treatment for Cancer

The methods of the invention may be used to identify a subpopulation of cancer patients, e.g., breast cancer patients, such as grade 1, 2, or 3 breast cancer patients, responsive to a treatment, e.g., anthracycline treatment, or other medical treatment. To this end, the level of expression of one or more (e.g., all) of the biomarkers in the CIN4 signature (HDGF, KIAA0286, RFC4, and MSH6) correlating to responsiveness to anthracycline treatment, may be determined so that patients responsive to anthracycline treatment may be identified.

Alternatively, genes may be identified as biomarkers (e.g., biomarkers in the CIN4 signature (HDGF, KIAA0286, RFC4, and MSH6)) according to their ability to discriminate patients known to be responsive to a treatment (e.g., anthracycline treatment) from those known to be resistant. The significance of the differences in gene (HDGF, KIAA0286, RFC4, and/or MSH6) expression between the responsive and resistant patients may be measured using, e.g., t-tests.

The patient populations (e.g., cancer patients, such as breast cancer patients (e.g., grade 1, 2, or 3 breast cancer patients)) considered may be further divided into patients predicted to survive without treatment (e.g., anthracycline treatment), patients predicted to die without treatment (e.g., anthracycline treatment), and patients predicted to have symptoms without treatment (e.g., anthracycline treatment). The above methodology may be similarly applied to any of these further defined patient subpopulations to identify biomarkers (e.g., biomarkers in the CIN4 signature (HDGF, KIAA0286, RFC4, and MSH6)) that are able to predict a patient's responsiveness to treatments, e.g., anthracycline treatment, or other treatments for cancer, e.g., breast cancer, such grade 1, 2, or 3 breast cancer.

Anthracycline and Non-Anthracycline Treatments

Patients with CIN4 signature scores that identify them as responsive to anthracycline treatment may be administered anthracycline treatment, which includes, but is not limited to, treatment with one or more of the following chemotherapeutic agents and their derivatives: epirubicin, daunorubicin, doxorubicin, idarubicin, valrubicin, actinomycin-D, bleomycin, mitomycin-C, and mitoxantrone.

Cancer patients with CIN4 signature scores identifying them as likely to be non-responsive to anthracycline treatment may be administered one or more chemotherapeutic agents other than an anthracycline. Some examples of non-anthracycline chemotherapeutic agents are listed in Table 2.

TABLE 2

| Therapeutic Class | Exemplary, Non-Limiting Agents |
|---|---|
| Alkylating Agents | Nitrogen mustards: such as mechlorethamine (nitrogen mustard), chlorambucil, cyclophosphamide (Cytoxan ®), ifosfamide, and melphalan Nitrosoureas: which include streptozocin, carmustine (BCNU), and lomustine<br>Alkyl sulfonates: busulfan<br>Triazines: dacarbazine (DTIC) and temozolomide (Temodar ®)<br>Ethylenimines: thiotepa and altretamine (hexamethylmelamine) |
| Antimetabolites | 5-fluorouracil (5-FU)<br>6-mercaptopurine (6-MP)<br>Capecitabine (Xeloda ®)<br>Cladribine<br>Clofarabine<br>Cytarabine (Ara-C ®)<br>Floxuridine<br>Fludarabine<br>Gemcitabine (Gemzar ®)<br>Hydroxyurea<br>Methotrexate<br>Pemetrexed (Alimta ®)<br>Pentostatin<br>Thioguanine |
| Topoisomerase inhibitors | topoisomerase I inhibitors<br>topotecan<br>irinotecan (CPT-11).<br>topoisomerase II inhibitors |

TABLE 2-continued

| Therapeutic Class | Exemplary, Non-Limiting Agents |
|---|---|
| | etoposide (VP-16) |
| | teniposide |
| Mitotic inhibitors | Taxanes such as paclitaxel (Taxol ®) and docetaxel (Taxotere ®) |
| | Epothilones: ixabepilone (Ixempra ®) |
| | Vinca alkaloids such as vinblastine (Velban ®), vincristine (Oncovin ®), and vinorelbine (Navelbine ®) |
| | Estramustine (Emcyt ®) |
| Corticosteroids | Examples include prednisone, methylprednisolone (Solumedrol ®), and dexamethasone (Decadron ®). |
| Miscellaneous Chemotherapeutics | L-asparaginase |
| | bortezomib (Velcade ®) |
| | imatinib (Gleevec ®) |
| | gefitinib (Iressa ®) |
| | sunitinib (Sutent ®) |
| Differentiating agents | retinoids |
| | tretinoin (ATRA or Atralin ®) |
| | bexarotene (Targretin ®) |
| | arsenic trioxide (Arsenox ®). |
| Hormone therapy | The anti-estrogens: fulvestrant (Faslodex ®), tamoxifen, and toremifene (Fareston ®) |
| | Aromatase inhibitors: anastrozole (Arimidex ®), exemestane (Aromasin ®), and letrozole (Femara ®) |
| | Progestins: megestrol acetate (Megace ®) |
| | Estrogens |
| | Anti-androgens: bicalutamide (Casodex ®), flutamide (Eulexin ®), and nilutamde (Nilandron ®) |
| | Gonadotropin-releasing hormone (GnRH), also known as luteinizing hormone-releasing hormone (LHRH) agonists or analogs: leuprolide (Lupron ®) and goserelin (Zoladex ®) |
| Immunotherapy | Monoclonal antibody therapy (passive immunotherapies), such as rituximab (Rituxan ®) and alemtuzumab (Campath ®) |
| | Non-specific immunotherapies and adjuvants (other substances or cells that boost the immune response), such as BCG, interleukin-2 (IL-2), and interferon-alfa |
| | Immunomodulating drugs, for instance, thalidomide and lenalidomide (Revlimid ®) |
| | Cancer vaccines (active specific immunotherapies) |

One or more of the above-mentioned chemotherapeutic agents may be administered to the appropriate patient populations identified based on their CIN4 scores using any methods known in the art, including but not limited to, oral, topical, transdermal, parenteral, subcutaneous, intranasal, intramuscular and intravenous routes, including both local and systemic applications. The chemotherapeutic agents, and pharmaceutical compositions thereof, may be administered to a patient in need thereof, for example, one or more times (e.g., 1-10 times or more) daily, weekly, monthly, biannually, annually, or as medically necessary. Dosages may be provided in either a single or multiple dosage regimens. Methods of administering chemotherapeutic agents are known in the art. See, for example, U.S. Pat. Nos. 7,811,998, 6,201,554, and 8,497,274, and U.S. Patent Application Publication Nos. US20090048301, WO2013025882, US20040063705, the disclosures of which are incorporated by reference in their entireties.

EXAMPLES

Example 1—BR9601 Clinical Trial

The BR9601 trial recruited 374 pre- and post-menopausal women with completely excised, histologically confirmed breast cancer and a clear indication for adjuvant chemotherapy. Patients were randomized between 8 cycles of CMF (i.v. cyclophosphamide 750 mg/m$^2$, methotrexate 50 mg/m$^2$, and 5-fluorouracil 600 mg/m$^2$) every 21 days, and E-CMF (4 cycles of epirubicin 100 mg/m$^2$ every 21 days followed by 4 cycles of the same CMF regimen). Patient characteristics are shown in Table 3. The protocol was approved by central and local ethics committees, and each patient provided written informed consent prior to randomization. For the current analysis, tissue blocks were retrieved and RNA was extracted.

Example 2—MA.5 Clinical Trial

The MA.5 trial randomized 716 premenopausal women with node-positive breast cancer to receive either adjuvant CEF or CMF. The CEF regimen consisted of 6 cycles of epirubicin 60 mg/m$^2$ and 5-fluorouracil (5-FU) 500 mg/m$^2$, both delivered intravenously on days 1 and 8, and oral cyclophosphamide 75 mg/m$^2$ daily on days 1 through 14. Patients randomized to the CEF regimen also received antibiotic prophylaxis throughout. The CMF regimen consisted of 6 cycles of methotrexate 40 mg/m$^2$ and 5-FU 600 mg/m$^2$, both delivered intravenously on days 1 and 8, and oral cyclophosphamide 100 mg/m$^2$ daily on days 1 through 14. Patient characteristics are shown in Table 3. The MA.5 protocol was approved by the institutional review board at each participating center and registered as NCI-V90-0027 on cancer.gov. Written informed consent was obtained from each woman.

TABLE 3

Baseline characteristics for patients from BR9601 and MA.5 clinical trials

| | Clinical trial | | CIN analysis | |
|---|---|---|---|---|
| | BR9601 | MA.5 | BR9601 | MA.5 |
| Number | 374 | 710 | 282 | 421 |
| Age Mean (range) | 50.6 (22.7-76.0) | 43.9 (23.4-57.2) | 50.6 (26.2-76.0) | 43.9 (23.4-57.2) |
| Treatment | | | | |
| E-CMF | 183 (48.9%) | 350 (49.3%) | 138 (48.9) | 208 (49.4%) |
| CMF | 191 (51.1%) | 360 (50.7%) | 144 (51.1%) | 213 (50.6%) |
| Size | | | | |
| <2.0 cm | 123 (32.9%) | 265 (37.9%) | 94 (33.3%) | 150 (36.1%) |
| >2.0 cm | 251 (67.1%) | 435 (62.1%) | 188 (66.7) | 265 (63.9%) |
| Missing | | 10 | | |
| Nodes | | | | |
| 0 | 48 (12.8%) | 0 | | |
| 1-3 | 214 (57.3%) | 433 (61.0%) | | |
| ≥4 | 112 (29.9%) | 277 (39.0%) | | |
| Grade | | | | |
| 1 | 22 (6.1%) | 77 (12.4%) | 19 (6.8%) | 42 (10.2%) |
| 2 | 126 (35.2%) | 204 (32.9%) | 96 (34.3%) | 120 (29.1%) |
| 3 | 210 (58.7%) | 340 (54.8%) | 165 (58.9%) | 250 (60.7%) |
| Unknown | 16 | 89 | 2 | 9 |

TABLE 3-continued

Baseline characteristics for patients
from BR9601 and MA.5 clinical trials

| | Clinical trial | | CIN analysis | |
|---|---|---|---|---|
| | BR9601 | MA.5 | BR9601 | MA.5 |
| ER Status | | | | |
| Positive | 202 (62.9%) | 424 (59.7%) | 155 (62.8%) | 253 (67.3%) |
| Negative | 119 (37.1%) | 200 (32.1%) | 92 (37.2%) | 123 (32.7%) |
| Unknown | 53 | 86 | 35 | 45 |

Example 3—RNA Purification and Gene Expression Analysis

Total RNA from formalin-fixed paraffin embedded (FFPE) tissue samples (2×10 μM sections) were extracted using the RecoverAll Total Nucleic Acid Isolation kit (Life Technologies) according to the manufacturers protocol and concentrations were determined using the NanoDrop ND-1000 spectrophotometer (NanoDrop Technologies).

RNA (400 ng) was used for the analysis with the nCounter system, according to the manufacturer's protocol (Nanostring® Technologies, Seattle, Wash., USA). In brief, 5 μl of RNA was hybridized at 96° C. overnight with the Nanostring Codeset.

Probes for the analysis of 70 genes and controls were synthesized by Nanostring technologies, including probes for the 70 genes of interest and 6 normalising genes. All 76 genes and controls were assayed simultaneously in multiplexed reactions (gene list, Table 4). After probe hybridizations and Nanostring nCounter digital reading, counts for each RNA species were extracted and analyzed. The nCounter CodeSet contains two types of built-in controls: positive controls (spiked RNA at various concentrations to assess the overall assay performance) and negative controls (alien probes for background calculation). To account for slight differences in hybridization and purification efficiency, the raw data were normalized to the standard curve generated via the nCounter system spike-in controls present in all reactions.

obtain hazard ratios for relapse or death. When comparing outcomes between the treatment arms within the groups of patients identified by biomarker expression, formal p-values were not calculated for sub-groups to avoid multiple testing and bias where one group was much smaller than the other. The Cox model was instead used to identify statistically significant interactions (p<0.05) between biomarkers and outcome on the different treatments (treatment by marker effect), in models that also included biomarker status (marker effect) and treatment, as covariates.

Example 5—Generation of CIN4 Score

The combined cohort was split to two groups according to the randomzied treatment. Using Affinity propagation clustering (R package apcluster[1]), the 70 genes were clustered into 9 groups according to their expression profiles. A multivariate Cox model was fit for each gene, adjusting for clinical variables including HER2, ER, PgR, tumor size, grade, and nodal status. The top genes from each expression cluster, with the most significant p-value in the anthracycline treated cohort and a non-significant CMF cohort, were selected to make a list of 21 genes. From this list, all possible combinations of 2,3,4, and 5 genes signatures were examined (210,1330,5985, and 20,349 combinations, respectively) and bootstrapped 100 times, with the median area under the curve (AUC) noted. In each bootstrap, the treatment cohort was split into 60% training and 40% test sets. The AUC was calculated from the test sets (R package survivalROC[2]). The gene signature selected had the greatest AUC and had four genes, termed the CIN4 signature. A multivariate Cox regression was fit using the four genes, adjusting for the same clinical variables mentioned above. A CIN4 score was generated using the expression values of the four genes, weighted by their regression coefficients.

Other Embodiments

All publications, patents, and patent applications mentioned in the above specification are hereby incorporated by reference. Various modifications and variations of the described methods and uses of the invention will be apparent to those skilled in the art without departing from the scope and spirit of the invention. Although the invention has been

TABLE 4

| CIN70 genes | | | | | | Housekeeping genes |
|---|---|---|---|---|---|---|
| DHCR7 | CCNB2 | ch-TOG | RNASEH2A | AURKB | ATM | GUSB |
| GPIandMGC13096 | FEN1 | MSH6 | RRM1 | CDC2 | ATR | PUM1 |
| CKS2 | FLJ10036 | PCNA | RRM2 | MAD2L1 | CDC25B | SF3A1 |
| BRRN1 | H2AFX | RAD21 | TGIF2 | PRC1 | CDC25C | TBP |
| CNAP1 | H2AFZ | RFC4 | ATAD2 | TPX2 | CHEK1 | TFRC |
| MCM10 | HDGF | UNG | NDUFAB1 | TTK | CHEK2 | TMED10 |
| CDC20 | KIF4A | CDC45L | KIAA0286 | UBE2C | MDM2 | |
| ESPL1 | PTTG1 | CDC6 | KIF20A | ZWINT | P53 | |
| FOXM1 | AURKA | CDCA8 | CDC3A | CMAS | CDKN1A | |
| MTB | MELK | CEP55 | ACTL6A | DKC1 | | |
| NEK2 | RAD51AP1 | CTPS | LSM4 | TRIP13 | | |
| OIP5 | TOPK | ECT2 | SFRS2 | CCT5 | | |
| TOP2A | EZH2 | MCM2 | ELAV1 | MTCH2 | | |
| CCNB1 | ASF1B | MCM7 | NXT1 | NUP205 | | |

Example 4—Statistical Analysis

The SPSS (v20) statistical package was used for statistical analysis. Kaplan-Meier estimates of survival were used for analysis of relapse free survival (RFS) and overall survival (OS). The Cox's proportional hazard model was used to described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

APPENDIX

Sequences

SEQ ID NO: 1 is the nucleic acid sequence of HDGF (GenBank: NM_004494.2).

SEQ ID NO: 1

```
   1 gagggaggag gaggagtggg gaccgggcgg ggggtggagg aagaggcctc gcgcagagga
  61 gggagcaatt gaatttcaaa cacaaacaac tgcacgagcg cgcacccacc gcgccggagc
 121 cttgccccga tccgcgcccg ccccgtccgt gcggcgcgcg ggcggagacg ccgtggccgc
 181 gccggagctc gggccggggg ccaccatcga ggcggggggcc gcgcgagggc cggagcggag
 241 cggcgccgcc accgccgcac gcgcaaactt gggctcgcgc ttcccggccc ggcgcggagc
 301 ccggggcgcc cggagccccg ccatgtcgcg atccaaccgg cagaaggagt acaaatgcgg
 361 ggacctggtg ttcgccaaga tgaagggcta cccacactgg ccggcccgga ttgacgagat
 421 gcctgaggct gccgtgaaat caacagccaa caataccaa gtcttttttt tcgggaccca
 481 cgagacggca ttcctgggcc ccaaagacct cttcccttac gaggaatcca aggagaagtt
 541 tggcaagccc aacaagagga aagggttcag cgaggggctg tgggagatcg agaacaaccc
 601 tactgtcaag gcttccggct atcagtcctc ccagaaaaag agctgtgtgg aagagcctga
 661 accagagccc gaagctgcag agggtgacgg tgataagaag gggaatgcag agggcagcag
 721 cgacgaggaa gggaagctgg tcattgatga gccagccaag gagaagaacg agaaaggagc
 781 gttgaagagg agagcagggg acttgctgga ggactctcct aaacgtccca aggaggcaga
 841 aaaccctgaa ggagaggaga aggaggcagc caccttggag gttgagaggc cccttcctat
 901 ggaggtggaa aagaatagca ccccctctga gcccggctct ggccgggggc ctccccaaga
 961 ggaagaagaa gaggaggatg aagaggaaga ggctaccaag gaagatgctg aggccccagg
1021 catcagagat catgagagcc tgtagccacc aatgtttcaa gaggagcccc caccctgttc
1081 ctgctgctgt ctgggtgcta ctggggaaac tggccatggc ctgcaaactg ggaaccccctt
1141 tcccacccca acctgctctc ctcttctact cacttttccc actccaagcc cagcccatgg
1201 agattgacct ggatggggca ggccacctgg ctctcacctc taggtcccca tactcctatg
1261 atctgagtca gagccatgtc ttctcctgg aatgagttga ggccactgtg ttccttccgc
1321 ttggagctat tttccaggct tctgctgggg cctgggacaa ctgctcccac ctcctgacac
1381 ccttctccca ctctcctagg cattctggac ctctgggttg ggatcagggg taggaatgga
1441 aaggatggag catcaacagc agggtgggct tgtggggcct gggagggca atcctcaaat
1501 gcggggtggg ggcagcacag gagggcggcc tccttctgag ctcctgtccc ctgctacacc
1561 tattatccca gctgcctaga ttcagggaaa gtgggacagc ttgtagggga ggggctcctt
1621 tccataaatc cttgatgatt gacaacaccc attttcctt ttgccgaccc caagagtttt
1681 gggagttgta gttaatcatc aagagaattt ggggcttcca agttgttcgg gccaaggacc
1741 tgagacctga agggttgact ttacccattt gggtgggagt gttgagcatc tgtcccccctt
1801 tagatctctg aagccacaaa taggatgctt gggaagactc ctagctgtcc tttttcctct
1861 ccacacagtg ctcaaggcca gcttatagtc atatatatca cccagacata aggaaaaga
1921 cacattttt aggaaatgtt tttaataaaa gaaaattaca aaaaaaaatt ttaaagaccc
1981 ctaaccctt gtgtgctctc cattctgctc cttccccatc gttgccccca tttctgaggt
2041 gcactgggag gctcccctc tatttggggc ttgatgactt tctttttgta gctgggggctt
2101 tgatgttcct tccagtgtca tttctcatcc acatacccctg acctggcccc ctcagtgttg
2161 tcaccagatc tgatttgtaa cccactgaga ggacagagag aaaataagtgc cctctcccac
2221 cctcttccta ctggtctctc tatgcctctc tacagtctcg tctcttttac cctggcccct
```

APPENDIX-continued

Sequences 2281 ctcccttggg ctctgatgaa aaattgctga ctgtagcttt ggaagtttag ctctgagaac 2341 cgtagatgat ttcagttcta ggaaaataaa acccgttgat tactataaaa aaaaaaa SEQ ID NO: 2 is the nucleic acid sequence of KIAA0286 (GenBank: NM_015257.2).

SEQ ID NO: 2

1 agttgctggg gtaaggcacg tgaggaggag gtggcttgag gcaaccatgg cgggaggaat 61 gaaagtggcg gtctcgccgg cagttggtcc cgggccctgg ggctcgggag tcggggcgg 121 tgggacagtg cggctactct tgatcctctc cggctgcttg gtctacggca cagctgaaac 181 tgatgtaaat gtggtcatgc ttcaggaatc ccaagtttgt gaaaagcgtg ccagccaaca 241 attctgttac acaaatgtgc ttatcccaaa atggcatgat atatggacac ggatacagat 301 ccgagtaaat agttccagat tggttcgagt cacccaggtg gagaatgagg agaaactgaa 361 ggagctagag caaagtcaaa ttttctacta ctctactggg atgactgtgg gaattgtggc 421 ctctctgcta atcatcattt ttatactatc taagtttatg cctaagaaaa gtcccattta 481 cgtcatcctg gtgggaggct ggtctttttc tctgtacctc attcaactag tttttaaaaa 541 tttacaagag atctggaggt gttactggca gtatcttta agttatgtcc tcacagttgg 601 attcatgagt tttgcagtat gttacaagta tgggcccttg gagaatgaac gaagtatcaa 661 cctgctgacc tggaccttgc agctgatggg cctgtgtttc atgtattctg gcatccagat 721 accacatatt gcccttgcca ttatcatcat tgctctttgt actaagaacc tggaacaccc 781 tattcagtgg ctgtacatca cctgcagaaa ggtgtgtaag ggagcagaaa agcctgttcc 841 ccctcgtctc ctgacagaag aagaatatcg gatacaagga gaggtagaaa cccgaaaggc 901 tttagaggag ctccgagaat tttgtaacag tccagactgc tctgcttgga agactgtttc 961 tcgaatccag tctccaaaaa gatttgctga ctttgtggaa ggctcttccc acctcacgcc 1021 aaatgaagtt tctgtccatg agcaggagta tggattaggg agcattattg cccaggatga 1081 aatctatgag gaagcatcct ctgaggagga ggactcatat tctcggtgtc ctgctatcac 1141 acagaacaac tttctaacct aggtagtggt cagttatctt tacgtggact ggcttggtgc 1201 cttggtccat gttgcatgtg ttgtgcaatt gctttcaacc ctttgaaaca gagtgagata 1261 gatagggtag aaattctcct actgaaataa gaggcctaaa aaggcctccc tttggaaatg 1321 ggaggtctct atgggatccc tgaggaagga gagtggataa agtagtgaat gctgggtagt 1381 tcacttccca ttggttaagc taacagccca ctttatgtt tccagagaaa ttggatggcc 1441 acagctagca tggcattcta gctccttctt gaaagttgat tcaatcatgg catttctgtc 1501 actggctggc tctccaaagt aagaactgtt gttaagtgca ggaatgcttt tagactatag 1561 gctgcaactt ccagagagaa atccacaaat ctgagcctcc ttcactccag cttttatttc 1621 agtgacttta gaataattat tgatttaact gttttgggag gaaaatagat ttttattgtt 1681 ttgttttta aatgaatgtc ttttaaaaaa cataacaaac tcatgttcca gaaccagcaa 1741 gtgctccaga gtgacacacc ccctaggccc tacatatttt attaatatgg attatccatt 1801 aaagccccag gagctgttgt tttaagcttt gatttagttc tcatacatat gatagaaagt 1861 cctatttgcc tttaggaaca tgcctgtagg ctcttctgca ggtgagatgt actgggcttt 1921 ttattatatt caactttcaa ttccatctta aaaacattt gtattcttct cttcccattc 1981 ttccttaccc tgcctttgcc cttcaggaa gggtcagttc ccttacctgt gaactatgta 2041 tgttcagagt agcattattc ctgctagcta ggagaagtca tcttgtttag gggatttgga APPENDIX-continued Sequences

```
2101 tgcttttat acgttctcca ttttcctgtc attgggtcat gttatctttg agttgctatg
2161 aaatcaggaa actgtctcct tttccttcc cttcctttgt ctacatgctc tgtccattcc
2221 tttcagcctt ttctcaccac ccatactccc ccaaatctgg gtaatttta agccttgaaa
2281 ctatgtagtt tcttgataca caatttgtag ttatgcagca gccacaattt gcattgccag
2341 gaaataggct ccaggttatc ttcatgcctc tgggtgctca ttcagctgtc aagtttccat
2401 gaacttacac ttatttatga ttgcgtttct gacctgagat gtatgctgcc tgttattgca
2461 gtagcattag tttcagattc ttttgccatt gcaaagtacc ccttataaac cagcaatgtc
2521 atctgtgagg aagcaaattc tcaagtgtct gtcatttact tggttctttt tctttgtggt
2581 cttcacccctt atacccctgga aaagtctgta attaccttag ccaggaagat agatggtcat
2641 ggcaagcgca cagcaccaga cttactggct caccaagatg atggaaaaag gcagatgatt
2701 ttttaaaaag ccgtaatgac tcctttagac cagccattta gcgtggtaat ttgaaaggc
2761 ctagctccat tgcagacttc caaagggtca gctctgagac tgccctccag gtgggcagtt
2821 gattatttcc accagtgttt tccagagcct taaactgtcc taagtgacaa ctacctcagt
2881 tggcaggaaa gagacatata gtagaaagtg aaaaatgagc agtatttggg cagatgctat
2941 gggttacagt tgaagggtaa aaggaacttt acattgggaa acctttatac ccttgtgaat
3001 tatgtacatg gtaaaatgtt ctctctctac aaagaactat taaaacttct gaaatatact
3061 atttttacc ttatttatag aaattgagac ctagcatatt taagcataag tttatttaa
3121 aaaataattc aactcgtgca agtggtctca ggattctctg gagattttgg tgcctcccct
3181 acttagggag gtgatagctt gcctataagg gtgacttttc ctgatcatgt ctttatttca
3241 atgagaaagc actgtgaaat tgtgaaagat tctcctcttt ctctgtttaa taaaccccca
3301 tgaaatatag tttccatctc tagaccagtt ttttttccac cgtgtttaga cttgaggtga
3361 ataaaatcaa actgtttttt actccctatc tggtagttgg agacctgagc tgtaggcagt
3421 ggagatggca attggttctg cagcctgaga gttgctctca cacagtgaag gacggtgctg
3481 ctctggtgtg ctgtgtgtcc ttgccctgcc tgcctgtggc tctgcccaga tgcttcagat
3541 cctctgtgtt ccggagattg cttgacttca accttcttta ggagctgctc ttgtctccct
3601 cttggccact tagtttgctg gctcagtcac tacttgaaga ccccatttaa ttttctctg
3661 gcagttatag ctcttgtgat ttcagtacag tctcatctct cagaccaatc tcatcaagaa
3721 ggattgaagg gataactatg aggtaagctg gacattggag ccgtgtttgc tgccacgtca
3781 gcgtcttgct gggtgaatgt caagccataa atgggctcca gggctctgga tctcatcagc
3841 attggaaatc tattgcctct catcagtctg accaaattat gtagagcatt aatgtagaga
3901 ctcccattaa tgggaataca agaggcagct ggcataaaac atttctttca ctttcctttc
3961 ccactcagat tgcttcaaga gaccaacaga acacagggat caaaaacaag gaaaatttag
4021 caacttcatt accttctaat aagtaattcc tgttagccac tgcatcccac caaaactagt
4081 ttattttcc cctcaaattc atgattttta cgtctgttac aaagggaatt ttgctgatag
4141 ctctttgggt cccactgttc cattttatgc taatagattc cattctaggg cccagccgtc
4201 tcttgactga tggtgttccc tttaacccctt ggcatgtata atagaatttt ggtgaatgaa
4261 agaacccaaa taggccagat agtcccccca ggccctgata tccataaaag gcttgggaat
4321 gcattatgta attgtcctta gtcttttgt tgttttagaa aaaaaaaca agatgggctc
4381 agatggatgc ctacgtaaaa atggttccta gctgtgtact cataacttt ctttgaattg
```

APPENDIX-continued

Sequences

```
4441 agtagtgaaa ggaaggagga ggaaaggaaa ttaaatgtcc ttctagtatt ctctggactc 4501 aagtctgaca tatgagataa taacctatat tgaaatgcca agaattgtat ctgaaacaag 4561 agaacagttt gacacattta tcatgccttc atattacata ttaactgaaa ccaattaata 4621 aacatatgaa atatccattg cacaaggcaa aggcacctaa acctttttgtt tcttttttcta 4681 catagcagaa attgattttt tttttattt ttagggggaa cctatataat tatgacccag 4741 tgatgtcttt tggtgactta agcttatgaa ttcaggttac aattgagttg attctagatg 4801 gttactacct tgaaaaggat gttggtgcct tatgtgacac gagccagagc ctgctgggaa 4861 taaacaaagc agattcatgc caacaccaac tcgtagcttt agtggcagat gggagtggtc 4921 acagactccc aaaatgtggg gctttggatt tccacaccat cccacgtgtg tgtcatcttc 4981 ctctttcaca ctcttgatga taatttgaaa atggtgaaat cacctctgaa tttgcctata 5041 gcatgagcac attcttatga caacataaca aatagttcat aatgtgaata ttagaaactg 5101 ttacagcctg cagttaccat aattttccat gtttgtggaa ttgatattga aatagcaggg 5161 ctaaggaatt actggcaagt tttagcctgt gggtaatacc ttaggggttat ttaaatatt 5221 gtaattttat ttaaatgttc atgaatgttt gaaaggaaca aaattatcag ggatggctct 5281 ttgccatggg tcttattttc accctctttt ctgtaagaaa aaagaacaat gtcttaatgt 5341 attttttaaag tttttggtat agtttctaat tccaattta ataaaagttt tatagataaa 5401 aaaaaaaaaa aaa
```

SEQ ID NO: 3 is the nucleic acid sequence of RFC4 (GenBank: NM_181573.2).

SEQ ID NO: 3

```
   1 cgcgctcacg tctgaagtgg gagcaatgca ccgggacagg gacacctcct aggccatgcc 61 tgttccagtc cagttctgcc tgaaagtccg gctggctcat cacctgccta aataaaaccg 121 tatacgggca aactccctcc gcaagcagcg cgccccagca ccggaagtga cgcgttacgt 181 gcccgcgtat tcctaccggc gtattcccgc cctgcttttc gcccgccgtt ccgtggcggg 241 aactgaggcg actgtgggga catcagtgat cggtgaagta ccatgcaagc atttcttaaa 301 ggtacatcca tcagtactaa accccgctg accaaggatc gaggagtagc tgccagtgcg 361 ggaagtagcg gagagaacaa gaaagccaaa cccgttccct gggtggaaaa atatcgccca 421 aaatgtgtgg atgaagttgc tttccaggaa gaagtggttg cagtgctgaa aaaatcttta 481 gaaggagcag atcttcctaa tctcttgttt tacggaccac ctggaactgg aaaaacatcc 541 actattttgg cagcagctag agaactcttt gggcctgaac ttttccgatt aagagttctt 601 gagttaaatg catctgatga acgtggaata caagtagttc gagagaaagt gaaaaattt 661 gctcaattaa ctgtgtcagg aagtcgctca gatgggaagc cgtgtccgcc ttttaagatt 721 gtgattctgg atgaagcaga ttctatgacc tcagctgctc aggcagcttt aagacgtacc 781 atggagaagg agtcgaaaac cacccgattc tgtcttatct gtaactatgt cagtcgaata 841 attgaacccc tgacctctag atgttcaaaa ttccgcttca agcctctgtc agataaaatt 901 caacagcagc gattactaga cattgccaag aaggaaaatg tcaaaattag tgatgaggga 961 atagcttatc ttgttaaagt gtcagaagga gacttaagaa agccattac atttcttcaa 1021 agcgctactc gattaacagg tggaaaggag atcacagaga agtgattac agacattgcc 1081 ggggtaatac cagctgagaa aattgatgga gtatttgctg cctgtcagag tggctctttt 1141 gacaaactag aagctgtggt caaggattta atagatgagg gtcatgcagc aactcagctc 1201 gtcaatcaac tccatgatgt ggttgtagaa aataacttat ctgataaaca gaagtctatt
```

APPENDIX-continued

Sequences

```
1261 atcacagaaa aacttgccga agttgacaaa tgcctagcag atggtgctga tgaacatttg
1321 caactcatca gcctttgtgc aactgtgatg cagcagttat ctcagaattg ttaacgtgaa
1381 tatatctgga tggggggttt tgtaaataat gaagttgtaa taaaaataaa atgaccaaaa
1441 gcacctttaa aaaaaaaaaa aaaaaaaaaa aaaaaaaaaa aaaaaa
```

SEQ ID NO: 4 is the nucleic acid sequence of MSH6 (GenBank NM_000179.1).

SEQ ID NO: 4

```
   1 atttcccgcc agcaggagcc gcgcggtaga tgcggtgctt ttaggagctc cgtccgacag
  61 aacggttggg ccttgccggc tgtcggtatg tcgcgacaga gcaccctgta cagcttcttc
 121 cccaagtctc cggcgctgag tgatgccaac aaggcctcgg ccagggcctc acgcgaaggc
 181 ggccgtgccg ccgctgcccc cggggcctct ccttccccag gcggggatgc ggcctggagc
 241 gaggctgggc ctgggcccag gcccttggcg cgatccgcgt caccgcccaa ggcgaagaac
 301 ctcaacggag ggctgcggag atcggtagcg cctgctgccc ccaccagttg tgacttctca
 361 ccaggagatt tggtttgggc caagatggag ggttacccct ggtggccttg tctggtttac
 421 aaccacccct ttgatggaac attcatccgc gagaagggga aatcagtccg tgttcatgta
 481 cagttttttg atgacagccc aacaagggg tgggttagca aaaggctttt aaagccatat
 541 acaggttcaa atcaaagga gcccagaag ggaggtcatt tttacagtgc aaagcctgaa
 601 atactgagag caatgcaacg tgcagatgaa gccttaaata aagacaagat taagaggctt
 661 gaattggcag tttgtgatga gccctcagag ccagaagagg aagaagagat ggaggtaggc
 721 acaacttacg taacagataa gagtgaagaa gataatgaaa ttgagagtga agaggaagta
 781 cagcctaaga cacaaggatc taggcgaagt agccgccaaa taaaaaaacg aagggtcata
 841 tcagattctg agagtgacat tggtggctct gatgtggaat ttaagccaga cactaaggag
 901 gaaggaagca gtgatgaaat aagcagtgga gtggggggata gtgagagtga aggcctgaac
 961 agccctgtca aagttgctcg aaagcggaag agaatggtga ctggaaatgg ctctcttaaa
1021 aggaaaagct ctaggaagga aacgccctca gccaccaaac aagcaactag catttcatca
1081 gaaaccaaga atactttgag agctttctct gcccctcaaa attctgaatc ccaagcccac
1141 gttagtggag gtggtgatga cagtagtcgc cctactgttt ggtatcatga aacttagaa
1201 tggcttaagg aggaaaagag aagagatgag cacaggagga ggcctgatca ccccgatttt
1261 gatgcatcta cactctatgt gcctgaggat ttcctcaatt cttgtactcc tgggatgagg
1321 aagtggtggc agattaagtc tcagaacttt gatcttgtca tctgttacaa ggtggggaaa
1381 ttttatgagc tgtaccacat ggatgctctt attggagtca gtgaactggg gctggtattc
1441 atgaaaggca actgggccca ttctggcttt cctgaaattg catttggccg ttattcagat
1501 tccctggtgc agaagggcta taaagtagca cgagtggaac agactgagac tccagaaatg
1561 atggaggcac gatgtagaaa gatggcacat atatccaagt atgatagagt ggtgaggagg
1621 gagatctgta ggatcattac caagggtaca cagacttaca gtgtgctgga aggtgatccc
1681 tctgagaact acagtaagta tcttcttagc ctcaaagaaa agaggaaga ttcttctggc
1741 catactcgtg catatggtgt gtgctttgtt gatacttcac tgggaaagtt tttcataggt
1801 cagttttcag atgatcgcca ttgttcgaga tttaggactc tagtggcaca ctatcccca
1861 gtacaagttt tatttgaaaa aggaaatctc tcaaaggaaa ctaaaacaat tctaaagagt
1921 tcattgtcct gttctcttca ggaaggtctg ataccccggct cccagttttg ggatgcatcc
```

APPENDIX-continued

Sequences

```
1981 aaaactttga gaactctcct tgaggaagaa tattttaggg aaaagctaag tgatggcatt 2041 ggggtgatgt taccccaggt gcttaaaggt atgacttcag agtctgattc cattgggttg 2101 acaccaggag agaaaagtga attggccctc tctgctctag gtggttgtgt cttctacctc 2161 aaaaaatgcc ttattgatca ggagctttta tcaatggcta attttgaaga atatattccc 2221 ttggattctg acacagtcag cactacaaga tctggtgcta tcttcaccaa agcctatcaa 2281 cgaatggtgc tagatgcagt gacattaaac aacttggaga tttttctgaa tggaacaaat 2341 ggttctactg aaggaaccct actagagagg gttgatactt gccatactcc ttttggtaag 2401 cggctcctaa agcaatggct ttgtgcccca ctctgtaacc attatgctat taatgatcgt 2461 ctagatgcca tagaagacct catggttgtg cctgacaaaa tctccgaagt tgtagagctt 2521 ctaaagaagc ttccagatct tgagaggcta ctcagtaaaa ttcataatgt tgggtctccc 2581 ctgaagagtc agaaccaccc agacagcagg gctataatgt atgaagaaac tacatacagc 2641 aagaagaaga ttattgattt tctttctgct ctggaaggat tcaaagtaat gtgtaaaatt 2701 atagggatca tggaagaagt tgctgatggt tttaagtcta aaatccttaa gcaggtcatc 2761 tctctgcaga caaaaaatcc tgaaggtcgt tttcctgatt tgactgtaga attgaaccga 2821 tgggatacag cctttgacca tgaaaaggct cgaaagactg gacttattac tcccaaagca 2881 ggctttgact ctgattatga ccaagctctt gctgacataa gagaaaatga acagagcctc 2941 ctggaatacc tagagaaaca gcgcaacaga attggctgta ggaccatagt ctattggggg 3001 attggtagga accgttacca gctggaaatt cctgagaatt tcaccactcg caatttgcca 3061 gaagaatacg agttgaaatc taccaagaag ggctgtaaac gatactggac caaaactatt 3121 gaaaagaagt tggctaatct cataaatgct gaagaacgga gggatgtatc attgaaggac 3181 tgcatgcggc gactgttcta taactttgat aaaaattaca aggactggca gtctgctgta 3241 gagtgtatcg cagtgttgga tgttttactg tgcctggcta actatagtcg aggggtgat 3301 ggtcctatgt gtcgcccagt aattctgttg ccggaagata ccccccctt cttagagctt 3361 aaaggatcac gccatccttg cattacgaag actttttttg gagatgattt tattcctaat 3421 gacattctaa taggctgtga ggaagaggag caggaaaatg gcaaagccta ttgtgtgctt 3481 gttactggac caaatatggg gggcaagtct acgcttatga gacaggctgg cttattagct 3541 gtaatggccc agatggggttg ttacgtccct gctgaagtgt gcaggctcac accaattgat 3601 agagtgttta ctagacttgg tgcctcagac agaataatgt caggtgaaag tacattttt 3661 gttgaattaa gtgaaactgc cagcatactc atgcatgcaa cagcacattc tctggtgctt 3721 gtggatgaat taggaagagg tactgcaaca tttgatggga cggcaatagc aaatgcagtt 3781 gttaaagaac ttgctgagac tataaaatgt cgtacattat tttcaactca ctaccattca 3841 ttagtagaag attattctca aaatgttgct gtgcgcctag acatatggc atgcatggta 3901 gaaaatgaat gtgaagaccc cagccaggag actattacgt tcctctataa attcattaag 3961 ggagcttgtc ctaaaagcta tggctttaat gcagcaaggc ttgctaatct cccagaggaa 4021 gttattcaaa agggacatag aaaagcaaga gaatttgaga agatgaatca gtcactacga 4081 ttatttcggg aagtttgcct ggctagtgaa aggtcaactg tagatgctga agctgtccat
```

APPENDIX-continued

Sequences

```
4141 aaattgctga ctttgattaa ggaattatag actgactaca ttggaagctt tgagttgact 4201 tctgaccaaa ggtggtaaat tcagacaaca ttatgatcta ataaacttta tttttaaaa 4261 atga
```

Other embodiments are within the following claims.

The invention claimed is:

1. A method of treating a cancer patient comprising
a) obtaining the results of a test that determined the level of expression of biomarkers having at least 25 consecutive nucleotides of the sequences of each of SEQ ID NOs: 1-4 in a sample from the cancer patient, and compared:
   i) the levels of expression of the biomarkers in the sample from the cancer patient to the levels of expression of the same biomarkers in a sample from a first reference patient known to be responsive to anthracycline treatment, or
   ii) the levels of expression of the biomarkers in the sample from the cancer patient to the levels of expression of the same biomarkers in a sample from a second reference patient known to be non-responsive to anthracycline treatment, and
   wherein said results show that:
   iii) the levels of expression of the biomarkers in the sample from the cancer patient are similar to the levels of expression of the biomarkers in the sample from the first reference patient or
   iv) the levels of expression of the biomarkers in the sample from the cancer patient are dissimilar to the levels of expression of the biomarkers in the sample from the second reference patient; and
(b) administering anthracycline treatment to the cancer patient;
wherein the biomarkers are HDGF, KIAA0286, RFC4, and MSH6.

2. The method of claim 1, wherein the sample from the cancer patient is a tissue sample.

3. The method of claim 2, wherein the sample from the cancer patient is a tumor sample.

4. The method of claim 1, wherein the cancer is a breast cancer.

5. The method of claim 4, wherein the cancer is grade 1, 2, or 3.

6. The method of claim 1, wherein:
(a) said obtaining occurs after said patient has received a first cancer treatment;
(b) said obtaining occurs after said patient has received a second cancer treatment.

7. The method of claim 6, wherein:
(a) said first cancer treatment comprises one or more of surgery, radiation therapy, and chemotherapy;
(b) said first or second cancer treatment comprises one or more of surgery, radiation therapy, and chemotherapy; or
(c) said second cancer treatment comprises one or more of surgery, radiation therapy, and chemotherapy.

8. The method of claim 1, wherein the level of expression of said biomarkers in said sample from the cancer patient, in said sample from said first reference patient, and in said sample from said second reference patient is determined by collecting nucleic acid molecules from said sample from the cancer patient.

9. The method of claim 1, wherein said anthracycline is selected from the group consisting of epirubicin, daunorubicin, doxorubicin, idarubicin, valrubicin, actinomycin-D, bleomycin, mitomycin-C, and mitoxantrone.

10. The method of claim 9, wherein said anthracycline is epirubicin.

11. The method of claim 1, further comprising treating said cancer patient with one or more chemotherapeutic agents listed in Table 2.

12. The method of claim 1, wherein said levels of expression of said biomarkers is determined using a microarray device.

13. The method of claim 1, wherein said method comprises determining the levels of expression of said biomarkers using a qRT-PCR.

14. A method of treating a cancer, said method comprising administering an anthracycline to a cancer patient that has been determined to have similar levels of expression of biomarkers having at least 25 consecutive nucleotides of the sequences of each of SEQ ID NOs: 1-4 relative to the levels of expression of the same biomarkers in a first reference patient known to be responsive to anthracycline treatment; wherein the biomarkers are HDGF, KIAA0286, RFC4, and MSH6.

15. The method of claim 14, wherein said anthracycline is selected from the group consisting of epirubicin, daunorubicin, doxorubicin, idarubicin, valrubicin, actinomycin-D, bleomycin, mitomycin-C, and mitoxantrone.

16. The method of claim 15, wherein said anthracycline is epirubicin.

17. The method of claim 14, wherein said cancer patient has been determined to have similar levels of expression of the biomarkers relative to the levels of expression of the same biomarkers in a first reference patient known to be responsive to anthracycline treatment by:
   a) determining the levels of expression of the biomarkers in a sample from the cancer patient, and
   b) i) comparing the levels of expression of the biomarkers in the sample from the cancer patient to the levels of expression of the same biomarkers in a sample from a first reference patient known to be responsive to anthracycline treatment, or
      ii) comparing the levels of expression of the biomarkers in the sample from the cancer patient to the levels of expression of the same biomarkers in a sample from a second reference patient known to be non-responsive to anthracycline treatment.

18. A method for treating a cancer patient comprising administering an anthracycline to a patient in which the levels of expression in a sample from the patient biomarkers having at least 25 consecutive nucleotides of the sequences of each of SEQ ID NOs: 1-4 has been determined to be similar to the levels of expression of said biomarkers in a reference patient known to be responsive to anthracycline treatment, wherein said levels of expression are determined using a device comprising at least four single-stranded nucleic acid molecules, each having at least 85% identity to a target nucleic acid molecule having a sequence that is complementary or identical to at least 5 consecutive nucleotides of said biomarkers respectively, wherein said at least four single-stranded nucleic acid molecules are sufficient for the detection of the levels of expression of said biomarkers and allow specific hybridization between said single stranded nucleic acid molecules and said target nucleic acid molecules, wherein the levels of expression of said biomarkers are predictive of responsiveness of said cancer patient to anthracycline treatment; wherein the biomarkers are HDGF, KIAA0286, RFC4, and MSH6.

19. The method of claim 18, wherein the target nucleic acid molecule has a sequence that is complementary or identical to at least 10 to 100, at least 20 to 100, at least 30 to 100, at least 40 to 100, at least 50 to 100, at least 60 to 100, at least 70 to 100, at least 80 to 100, or at least 90 to 100 consecutive nucleotides.

20. The method of claim 18, wherein said at least one single-stranded nucleic acid molecule has a length in the range of 10 to 100 nucleotides.

21. The method of claim 18, said device allowing, when contacted with a diverse population of nucleic acid molecules prepared from a sample under conditions allowing hybridization to occur, the determination of the levels of expression of said biomarkers.

22. The method of claim 18, wherein the device is a microarray device.

23. The method of claim 18, wherein the sample is a tissue sample.

24. The method of claim 23, wherein the sample is a tumor sample.

25. The method of claim 18, wherein the cancer is a breast cancer.

26. The method of claim 25, wherein the cancer is grade 1, 2, or 3.

27. The method of claim 18, wherein:
   (a) said administering occurs in said patient after said patient has received a first cancer treatment; or
   (b) said administering occurs in said patient after said patient has received a second cancer treatment.

28. The method of claim 27, wherein:
   (a) said first cancer treatment comprises any combination of one or more of surgery, radiation therapy, and chemotherapy;
   (b) said first cancer treatment comprises one or more of surgery, radiation therapy, and chemotherapy and combinations thereof;
   (c) said first or second cancer treatment comprises one or more of surgery, radiation therapy, and chemotherapy and combinations thereof; or
   (d) said second cancer treatment comprises one or more of surgery, radiation therapy, and chemotherapy and combinations thereof.

29. The method of claim 7, wherein said first or second cancer treatment is surgery.

30. The method of claim 8, further comprising detecting said nucleic acid molecules using one or more fluorescent probes or using a quantitative reverse transcription-polymerase chain reaction (qRT-PCR) to amplify said nucleic acid molecules.

31. The method of claim 1, wherein the biomarker comprises all or a portion of the sequences of each of SEQ ID NOs: 1-4.

32. The method of claim 1, wherein the biomarker consists of all or a portion of the sequences of each of SEQ ID NOs: 1-4.

33. The method of claim 14, wherein the biomarker comprises all or a portion of the sequences of each of SEQ ID NOs: 1-4.

34. The method of claim 14, wherein the biomarker consists of all or a portion of the sequences of each of SEQ ID NOs: 1-4.

* * * * *

SEQUENCE LISTING

<160> NUMBER OF SEQ ID NOS: 4

<210> SEQ ID NO 1
<211> LENGTH: 2397
<212> TYPE: DNA
<213> ORGANISM: Homo sapiens

<400> SEQUENCE: 1

```
gagggaggag gaggagtggg gaccgggcgg ggggtggagg aagaggcctc gcgcagagga      60
gggagcaatt gaatttcaaa cacaaacaac tgcacgagcg cgcacccacc gcgccggagc     120
cttgccccga tccgcgcccg ccccgtccgt gcggcgcgcg ggcggagacg ccgtggccgc     180
gccggagctc gggccggggg ccaccatcga ggcggggggcc gcgcgagggc cggagcggag     240
cggcgccgcc accgccgcac gcgcaaactt gggctcgcgc ttcccggccc ggcgcggagc     300
ccggggcgcc cggagccccg ccatgtcgcg atccaaccgg cagaaggagt acaaatgcgg     360
ggacctggtg ttcgccaaga tgaagggcta cccacactgg ccggcccgga ttgacgagat     420
gcctgaggct gccgtgaaat caacagccaa caaataccaa gtcttttttt tcgggaccca     480
cgagacggca ttcctgggcc ccaaagacct cttcccttac gaggaatcca aggagaagtt     540
tggcaagccc aacaagagga aagggttcag cgaggggctg tgggagatcg agaacaaccc     600
tactgtcaag gcttccggct atcagtcctc ccagaaaaag agctgtgtgg aagagcctga     660
accagagccc gaagctgcag agggtgacgg tgataagaag gggaatgcag agggcagcag     720
cgacgaggaa gggaagctgg tcattgatga gccagccaag gagaagaacg agaaaggagc     780
gttgaagagg agagcagggg acttgctgga ggactctcct aaacgtccca aggaggcaga     840
aaaccctgaa ggagaggaga aggaggcagc caccttggag gttgagaggc cccttcctat     900
ggaggtggaa aagaatagca ccccctctga gcccggctct ggccggggc ctccccaaga     960 ggaagaagaa gaggaggatg aagaggaaga ggctaccaag gaagatgctg aggccccagg    1020
catcagagat catgagagcc tgtagccacc aatgtttcaa gaggagcccc caccctgttc    1080
ctgctgctgt ctgggtgcta ctggggaaac tggccatggc ctgcaaactg gaacccctt    1140 tcccacccca acctgctctc ctcttctact cactttccc actccaagcc cagcccatgg    1200
agattgacct ggatggggca ggccacctgg ctctcacctc taggtcccca tactcctatg    1260
atctgagtca gagccatgtc ttctccctgg aatgagttga ggccactgtg ttccttccgc    1320
ttggagctat tttccaggct tctgctgggg cctgggacaa ctgctcccac ctcctgacac    1380
ccttctccca ctctcctagg cattctggac tctgggttg ggatcagggg taggaatgga    1440
aaggatggag catcaacagc agggtgggct tgtgggcct gggaggggca atcctcaaat    1500
gcggggtggg ggcagcacag gagggcggcc tccttctgag ctcctgtccc ctgctacacc    1560
tattatccca gctgcctaga ttcagggaaa gtgggacagc ttgtagggga ggggctcctt    1620
```

-continued

```
tccataaatc cttgatgatt  gacaacaccc  attttttcctt  ttgccgaccc  caagagtttt    1680
gggagttgta gttaatcatc  aagagaattt  ggggcttcca  agttgttcgg  gccaaggacc    1740
tgagacctga agggttgact  ttacccattt  gggtgggagt  gttgagcatc  tgtccccctt    1800
tagatctctg aagccacaaa  taggatgctt  gggaagactc  ctagctgtcc  ttttttcctct    1860
ccacacagtg ctcaaggcca  gcttatagtc  atatatatca  cccagacata  aaggaaaaga    1920
cacattttt  aggaaatgtt  tttaataaaa  gaaaattaca  aaaaaaaatt  ttaaagaccc    1980
ctaaccctt  gtgtgctctc  cattctgctc  cttccccatc  gttgccccca  tttctgaggt    2040
gcactgggag ctcccccttc  tatttggggc  ttgatgactt  tcttttttgta  gctgggggctt    2100
tgatgttcct tccagtgtca  tttctcatcc  acatacccctg  acctggcccc  ctcagtgttg    2160
tcaccagatc tgatttgtaa  cccactgaga  ggacagagag  aaataagtgc  cctctcccac    2220
cctcttccta ctggtctctc  tatgcctctc  tacagtctcg  tctcttttac  cctggcccct    2280
ctcccttggg ctctgatgaa  aaattgctga  ctgtagcttt  ggaagtttag  ctctgagaac    2340
cgtagatgat ttcagttcta  ggaaaataaa  acccgttgat  tactataaaa  aaaaaaa       2397
```

<210> SEQ ID NO 2
<211> LENGTH: 5413
<212> TYPE: DNA
<213> ORGANISM: Homo sapiens

<400> SEQUENCE: 2

```
agttgctggg gtaaggcacg tgaggaggag  gtggcttgag  gcaaccatgg  cgggaggaat    60
gaaagtggcg gtctcgccgg cagttggtcc  cgggccctgg  ggctcggag   tcggggggcgg    120
tgggacagtg cggctactct tgatcctctc  cggctgcttg  gtctacggca  cagctgaaac    180
tgatgtaaat gtggtcatgc ttcaggaatc  ccaagtttgt  gaaaagcgtg  ccagccaaca    240
attctgttac acaaatgtgc ttatcccaaa  atgcatgat   atatggacac  ggatacagat    300
ccgagtaaat agttccagat tggttcgagt  cacccaggtg  gagaatgagg  agaaactgaa    360
ggagctagag caaagtcaaa ttttctacta  ctctactggg  atgactgtgg  gaattgtggc    420
ctctctgcta atcatcattt ttatactatc  taagtttatg  cctaagaaaa  gtcccattta    480
cgtcatcctg gtgggaggct ggtcttttc   tctgtacctc  attcaactag  ttttttaaaaa    540
tttacaagag atctggaggt gttactggca  gtatcttta   agttatgtcc  tcacagttgg    600
attcatgagt tttgcagtat gttacaagta  tgggcccttg  gagaatgaac  gaagtatcaa    660
cctgctgacc tggaccttgc agctgatggg  cctgtgtttc  atgtattctg  gcatccagat    720
accacatatt gcccttgcca ttatcatcat  tgctctttgt  actaagaacc  tggaacaccc    780
tattcagtgg ctgtacatca cctgcagaaa  ggtgtgtaag  ggagcagaaa  agcctgttcc    840
ccctcgtctc ctgacagaag aagaatatcg  gatacaagga  gaggtagaaa  cccgaaaggc    900
tttagaggag ctccgagaat tttgtaacag  tccagactgc  tctgcttgga  agactgtttc    960
tcgaatccag tctccaaaaa gatttgctga  ctttgtggaa  ggctcttccc  acctcacgcc    1020
aaatgaagtt tctgtccatg agcaggagta  tggattaggg  agcattattg  cccaggatga    1080
aatctatgag gaagcatcct ctgaggagga  ggactcatat  tctcggtgtc  ctgctatcac    1140
acagaacaac tttctaacct aggtagtggt  cagttatctt  tacgtggact  ggcttggtgc    1200
cttggtccat gttgcatgtg ttgtgcaatt  gctttcaacc  cttttgaaaca  gagtgagata    1260
gatagggtag aaattctcct actgaaataa  gaggcctaaa  aaggcctccc  tttggaaatg    1320
ggaggtctct atgggatccc tgaggaagga  gagtggataa  agtagtgaat  gctgggtagt    1380
```

```
tcacttccca ttggttaagc taacagccca cttttatgtt tccagagaaa ttggatggcc    1440
acagctagca tggcattcta gctccttctt gaaagttgat tcaatcatgg catttctgtc    1500
actggctggc tctccaaagt aagaactgtt gttaagtgca ggaatgcttt tagactatag    1560
gctgcaactt ccagagagaa atccacaaat ctgagcctcc ttcactccag cttttatttc    1620
agtgacttta gaataattat tgatttaact gttttgggag gaaaatagat ttttattgtt    1680
ttgtttttta aatgaatgtc ttttaaaaaa cataacaaac tcatgttcca gaaccagcaa    1740
gtgctccaga gtgacacacc ccctaggccc ctacatattt attaatatgg attatccatt    1800
aaagccccag gagctgttgt tttaagcttt gatttagttc tcatacatat gatagaaagt    1860
cctatttgcc tttaggaaca tgcctgtagg ctcttctgca ggtgagatgt actgggcttt    1920
ttattatatt caactttcaa ttccatctta aaaacattt gtattcttct cttcccattc    1980
ttccttaccc tgcctttgcc ctttcaggaa gggtcagttc ccttacctgt gaactatgta    2040
tgttcagagt agcattattc ctgctagcta ggagaagtca tcttgtttag gggatttgga    2100 tgcttttat acgttctcca ttttcctgtc attgggtcat gttatctttg agttgctatg    2160
aaatcaggaa actgtctcct tttcctttcc cttcctttgt ctacatgctc tgtccattcc    2220
tttcagcctt ttctcaccac ccatactccc ccaaatctgg gtaatttta agccttgaaa    2280 ctatgtagtt tcttgataca caatttgtag ttatgcagca gccacaattt gcattgccag    2340
gaaataggct ccaggttatc ttcatgcctc tgggtgctca ttcagctgtc aagtttccat    2400
gaacttacac ttatttatga ttgcgtttct gacctgagat gtatgctgcc tgttattgca    2460
gtagcattag tttcagattc ttttgccatt gcaaagtacc ccttataaac cagcaatgtc    2520
atctgtgagg aagcaaattc tcaagtgtct gtcatttact tggttctttt tctttgtggt    2580 cttcacccctt ataccctgga aaagtctgta attaccttag ccaggaagat agatggtcat    2640
ggcaagcgca cagcaccaga cttactggct caccaagatg atggaaaaag gcagatgatt    2700
ttttaaaaag ccgtaatgac tcctttagac cagccattta gcgtggtaat tttgaaaggc    2760
ctagctccat tgcagacttc caaagggtca gctctgagac tgccctccag gtgggcagtt    2820
gattatttcc accagtgttt tccagagcct taaactgtcc taagtgacaa ctacctcagt    2880
tggcaggaaa gagacatata gtagaaagtg aaaaatgagc agtatttggg cagatgctat    2940
gggttacagt tgaagggtaa aaggaacttt acattgggaa acctttatac ccttgtgaat    3000
tatgtacatg gtaaaatgtt ctctctctac aaagaactat taaaacttct gaaatatact    3060
attttttacc ttatttatag aaattgagac ctagcatatt taagcataag tttatttttaa    3120 aaaataattc aactcgtgca agtggtctca ggattctctg gagattttgg tgcctcccct    3180
acttagggag gtgatagctt gcctataagg gtgactttc ctgatcatgt ctttatttca    3240
atgagaaagc actgtgaaat tgtgaaagat tctcctcttt ctctgtttaa taaaccccca    3300
tgaaatatag tttccatctc tagaccagtt ttttttccac cgtgtttaga cttgaggtga    3360
ataaaatcaa actgtttttt actccctatc tggtagttgg agacctgagc tgtaggcagt    3420
ggagatggca attggttctg cagcctgaga gttgctctca cacagtgaag gacggtgctg    3480
ctctggtgtg ctgtgtgtcc ttgccctgcc tgcctgtggc tctgcccaga tgcttcagat    3540
cctctgtgtt ccggagattg cttgacttca accttcttta ggagctgctc ttgtctccct    3600
cttggccact tagtttgctg gctcagtcac tacttgaaga ccccatttaa ttttttctctg    3660 gcagttatag ctcttgtgat ttcagtacag tctcatctct cagaccaatc tcatcaagaa    3720
```

```
ggattgaagg gataactatg aggtaagctg gacattggag ccgtgtttgc tgccacgtca      3780
gcgtcttgct gggtgaatgt caagccataa atgggctcca gggctctgga tctcatcagc      3840
attggaaatc tattgcctct catcagtctg accaaattat gtagagcatt aatgtagaga      3900
ctcccattaa tgggaataca agaggcagct ggcataaaac atttcttttca ctttcctttc      3960 ccactcagat tgcttcaaga gaccaacaga acacagggat caaaaacaag gaaaatttag      4020
caacttcatt accttctaat aagtaattcc tgttagccac tgcatcccac caaaactagt      4080
ttatttttcc cctcaaattc atgattttta cgtctgttac aaagggaatt ttgctgatag      4140
ctctttgggt cccactgttc cattttatgc taatagattc cattctaggg cccagccgtc      4200
tcttgactga tggtgttccc tttaaccctt ggcatgtata atagaatttt ggtgaatgaa      4260
agaacccaaa taggccagat agtccccca ggccctgata tccataaaag gctgggaat       4320 gcattatgta attgtcctta gtcttttgt tgttttagaa aaaaaaaaca agatgggctc       4380
agatggatgc ctacgtaaaa atggttccta gctgtgtact cataactttt ctttgaattg      4440
agtagtgaaa ggaaggagga ggaaaggaaa ttaaatgtcc ttctagtatt ctctggactc      4500
aagtctgaca tatgagataa taacctatat tgaaatgcca agaattgtat ctgaaacaag      4560
agaacagttt gacacattta tcatgccttc atattacata ttaactgaaa ccaattaata      4620
aacatatgaa atatccattg cacaaggcaa aggcacctaa acctttgtt tctttttcta       4680 catagcagaa attgattttt tttttatttt tttaggggaa cctatataat tatgacccag      4740
tgatgtcttt tggtgactta agcttatgaa ttcaggttac aattgagttg attctagatg      4800
gttactacct tgaaaaggat gttggtgcct tatgtgacac gagccagagc ctgctgggaa      4860
taaacaaagc agattcatgc caacaccaac tcgtagcttt agtggcagat gggagtggtc      4920
acagactccc aaaatgtggg gctttggatt tccacaccat cccacgtgtg tgtcatcttc      4980
ctctttcaca ctcttgatga taatttgaaa atggtgaaat cacctctgaa tttgcctata      5040
gcatgagcac attcttatga caacataaca aatagttcat aatgtgaata ttagaaactg      5100
ttacagcctg cagttaccat aattttccat gtttgtggaa ttgatattga aatagcaggg      5160
ctaaggaatt actggcaagt tttagcctgt gggtaatacc ttagggttat ttaaatattt      5220
gtaattttat ttaaatgttc atgaatgttt gaaaggaaca aaattatcag ggatggctct      5280
ttgccatggg tcttattttc accctctttt ctgtaagaaa aagaacaat gtcttaatgt        5340 attttttaaag tttttggtat agtttctaat tccaatttta ataaagtttt tatagataaa     5400
aaaaaaaaaa aaa                                                         5413

<210> SEQ ID NO 3
<211> LENGTH: 1486
<212> TYPE: DNA
<213> ORGANISM: Homo sapiens

<400> SEQUENCE: 3
cgcgctcacg tctgaagtgg gagcaatgca ccgggacagg gacacctcct aggccatgcc       60
tgttccagtc cagttctgcc tgaaagtccg gctggctcat cacctgccta ataaaaccg       120 tatacgggca aactccctcc gcaagcagcg cgccccagca ccggaagtga cgcgttacgt      180
gcccgcgtat tcctaccggc gtattcccgc cctgcttttc gcccgccgtt ccgtggcggg      240
aactgaggcg actgtgggga catcagtgat cggtgaagta ccatgcaagc atttcttaaa      300
ggtacatcca tcagtactaa accccgctg accaaggatc gaggagtagc tgccagtgcg       360
ggaagtagcg gagagaacaa gaaagccaaa cccgttccct gggtggaaaa atatcgccca      420
```

```
aaatgtgtgg atgaagttgc tttccaggaa gaagtggttg cagtgctgaa aaaatcttta      480
gaaggagcag atcttcctaa tctcttgttt tacggaccac ctggaactgg aaaaacatcc      540
actattttgg cagcagctag agaactcttt gggcctgaac ttttccgatt aagagttctt      600
gagttaaatg catctgatga acgtggaata caagtagttc gagagaaagt gaaaaatttt      660
gctcaattaa ctgtgtcagg aagtcgctca gatgggaagc cgtgtccgcc ttttaagatt      720
gtgattctgg atgaagcaga ttctatgacc tcagctgctc aggcagcttt aagacgtacc      780
atggagaagg agtcgaaaac cacccgattc tgtcttatct gtaactatgt cagtcgaata      840
attgaacccc tgacctctag atgttcaaaa ttccgcttca agcctctgtc agataaaatt      900
caacagcagc gattactaga cattgccaag aaggaaaatg tcaaaattag tgatgaggga      960
atagcttatc ttgttaaagt gtcagaagga gacttaagaa aagccattac atttcttcaa     1020
agcgctactc gattaacagg tggaaaggag atcacagaga aagtgattac agacattgcc     1080
ggggtaatac cagctgagaa aattgatgga gtatttgctg cctgtcagag tggctctttt     1140
gacaaactag aagctgtggt caaggattta atagatgagg gtcatgcagc aactcagctc     1200
gtcaatcaac tccatgatgt ggttgtagaa aataacttat ctgataaaca gaagtctatt     1260
atcacagaaa aacttgccga agttgacaaa tgcctagcag atggtgctga tgaacatttg     1320
caactcatca gcctttgtgc aactgtgatg cagcagttat ctcagaattg ttaacgtgaa     1380
tatatctgga tggggggttt tgtaaataat gaagttgtaa taaaaataaa atgaccaaaa     1440
gcacctttaa aaaaaaaaaa aaaaaaaaaa aaaaaaaaaa aaaaaa                     1486

<210> SEQ ID NO 4
<211> LENGTH: 4264
<212> TYPE: DNA
<213> ORGANISM: Homo sapiens

<400> SEQUENCE: 4
atttcccgcc agcaggagcc gcgcggtaga tgcggtgctt ttaggagctc cgtccgacag       60
aacggttggg ccttgccggc tgtcggtatg tcgcgacaga gcaccctgta cagcttcttc      120
cccaagtctc cggcgctgag tgatgccaac aaggcctcgg ccaggcctc acgcgaaggc      180 ggccgtgccg ccgctgcccc cggggcctct ccttccccag gcgggatgc ggcctggagc      240 gaggctgggc ctgggcccag gcccttggcg cgatccgcgt caccgcccaa ggcgaagaac      300
ctcaacggag ggctgcggag atcggtagcg cctgctgccc ccaccagttg tgacttctca      360
ccaggagatt tggtttgggc caagatggag ggttaccccct ggtggccttg tctggtttac      420
aaccacccct ttgatggaac attcatccgc gagaaaggga atcagtccg tgttcatgta      480 cagttttttg atgacagccc aacaaggggc tgggttagca aaaggctttt aaagccatat      540
acaggttcaa aatcaaagga agcccagaag ggaggtcatt tttacagtgc aaagcctgaa      600
atactgagag caatgcaacg tgcagatgaa gccttaaata agacaagat taagaggctt      660 gaattggcag tttgtgatga gccctcagag ccagaagagg aagaagagat ggaggtaggc      720
acaacttacg taacagataa gagtgaagaa gataatgaaa ttgagagtga agaggaagta      780
cagcctaaga cacaaggatc taggcgaagt agccgccaaa taaaaaaacg aagggtcata      840
tcagattctg agagtgacat tggtggctct gatgtggaat ttaagccaga cactaaggag      900
gaaggaagca gtgatgaaat aagcagtgga gtggggata gtgagagtga aggcctgaac      960
agccctgtca agttgctcg aaagcggaag agaatggtga ctggaaatgg ctctcttaaa     1020
```

```
aggaaaagct ctaggaagga aacgccctca gccaccaaac aagcaactag catttcatca    1080
gaaaccaaga atactttgag agctttctct gccccctcaaa attctgaatc ccaagcccac   1140
gttagtggag gtggtgatga cagtagtcgc cctactgttt ggtatcatga aactttagaa    1200
tggcttaagg aggaaaagag aagagatgag cacaggagga ggcctgatca ccccgatttt    1260
gatgcatcta cactctatgt gcctgaggat ttcctcaatt cttgtactcc tgggatgagg    1320
aagtggtggc agattaagtc tcagaacttt gatcttgtca tctgttacaa ggtggggaaa    1380
ttttatgagc tgtaccacat ggatgctctt attggagtca gtgaactggg gctggtattc    1440
atgaaaggca actgggccca ttctggcttt cctgaaattg catttggccg ttattcagat    1500
tccctggtgc agaagggcta taaagtagca cgagtggaac agactgagac tccagaaatg    1560
atggaggcac gatgtagaaa gatggcacat atatccaagt atgatagagt ggtgaggagg    1620
gagatctgta ggatcattac caagggtaca cagacttaca gtgtgctgga aggtgatccc    1680
tctgagaact acagtaagta tcttcttagc ctcaaagaaa aagaggaaga ttcttctggc    1740
catactcgtg catatggtgt gtgctttgtt gatacttcac tgggaaagtt tttcataggt    1800
cagttttcag atgatcgcca ttgttcgaga tttaggactc tagtggcaca ctatccccca    1860
gtacaagttt tatttgaaaa aggaaatctc tcaaaggaaa ctaaaacaat tctaaagagt    1920
tcattgtcct gttctcttca ggaaggtctg atacccggct cccagttttg ggatgcatcc    1980
aaaactttga gaactctcct tgaggaagaa tattttaggg aaaagctaag tgatggcatt    2040
ggggtgatgt tacccaggt gcttaaaggt atgacttcag agtctgattc cattgggttg     2100
acaccaggag agaaaagtga attggccctc tctgctctag gtggttgtgt cttctacctc    2160
aaaaaatgcc ttattgatca ggagctttta tcaatggcta attttgaaga atatattccc    2220
ttggattctg acacagtcag cactacaaga tctggtgcta tcttcaccaa agcctatcaa    2280
cgaatggtgc tagatgcagt gacattaaac aacttggaga ttttctgaa tggaacaaat     2340 ggttctactg aaggaaccct actagagagg gttgatactt gccatactcc ttttggtaag    2400
cggctcctaa agcaatggct ttgtgcccca ctctgtaacc attatgctat taatgatcgt    2460
ctagatgcca tagaagacct catggttgtg cctgacaaaa tctccgaagt tgtagagctt    2520
ctaaagaagc ttccagatct tgagaggcta ctcagtaaaa ttcataatgt tgggtctccc    2580
ctgaagagtc agaaccaccc agacagcagg gctataatgt atgaagaaac tacatacagc    2640
aagaagaaga ttattgattt tcttctctgct ctggaaggat tcaaagtaat gtgtaaaatt    2700
atagggatca tggaagaagt tgctgatggt tttaagtcta aaatccttaa gcaggtcatc    2760
tctctgcaga caaaaaatcc tgaaggtcgt tttcctgatt tgactgtaga attgaaccga    2820
tgggatacag cctttgacca tgaaaaggct cgaaagactg gacttattac tcccaaagca    2880
ggctttgact ctgattatga ccaagctctt gctgacataa gagaaatga acagagcctc     2940 ctggaatacc tagagaaaca gcgcaacaga attggctgta ggaccatagt ctatggggg    3000 attggtagga accgttacca gctggaaatt cctgagaatt tcaccactcg caatttgcca    3060
gaagaatacg agttgaaatc taccaagaag ggctgtaaac gatactggac caaaactatt    3120
gaaaagaagt tggctaatct cataaatgct gaagaacgga gggatgtatc attgaaggac    3180
tgcatgcggc gactgttcta taactttgat aaaaaattaca aggactggca gtctgctgta    3240
gagtgtatcg cagtgttgga tgttttactg tgcctggcta actatagtcg agggggtgat    3300
ggtcctatgt gtcgcccagt aattctgttg ccggaagata cccccccctt cttagagctt    3360
aaaggatcac gccatccttg cattacgaag actttttttg gagatgattt tattcctaat    3420
```

-continued

```
gacattctaa taggctgtga ggaagaggag caggaaaatg gcaaagccta ttgtgtgctt    3480
gttactggac caaatatggg gggcaagtct acgcttatga gacaggctgg cttattagct    3540
gtaatggccc agatgggttg ttacgtccct gctgaagtgt gcaggctcac accaattgat    3600
agagtgttta ctagacttgg tgcctcagac agaataatgt caggtgaaag tacatttttt    3660
gttgaattaa gtgaaactgc cagcatactc atgcatgcaa cagcacattc tctggtgctt    3720
gtggatgaat taggaagagg tactgcaaca tttgatggga cggcaatagc aaatgcagtt    3780
gttaaagaac ttgctgagac tataaaatgt cgtacattat tttcaactca ctaccattca    3840
ttagtagaag attattctca aaatgttgct gtgcgcctag gacatatggc atgcatggta    3900
gaaaatgaat gtgaagaccc cagccaggag actattacgt tcctctataa attcattaag    3960
ggagcttgtc ctaaaagcta tggctttaat gcagcaaggc ttgctaatct cccagaggaa    4020
gttattcaaa agggacatag aaaagcaaga gaatttgaga agatgaatca gtcactacga    4080
ttatttcggg aagtttgcct ggctagtgaa aggtcaactg tagatgctga agctgtccat    4140
aaattgctga ctttgattaa ggaattatag actgactaca ttggaagctt tgagttgact    4200
tctgaccaaa ggtggtaaat tcagacaaca ttatgatcta ataaacttta tttttttaaaa   4260 atga                                                                 4264
```